United States Patent
Callahan et al.

(10) Patent No.: US 12,337,072 B2
(45) Date of Patent: Jun. 24, 2025

(54) SYSTEMS AND METHODS FOR COOLING ULTRAVIOLET (UV) LAMPS

(71) Applicant: THE BOEING COMPANY, Chicago, IL (US)

(72) Inventors: Kevin S. Callahan, Everett, WA (US); Michael Kipling Klein, Bothell, WA (US); Christopher Edward Plass, Snohomish, WA (US)

(73) Assignee: The Boeing Company, Chicago, IL (US)

( * ) Notice: Subject to any disclaimer, the term of this patent is extended or adjusted under 35 U.S.C. 154(b) by 888 days.

(21) Appl. No.: 17/530,619

(22) Filed: Nov. 19, 2021

(65) Prior Publication Data

US 2022/0105212 A1    Apr. 7, 2022

Related U.S. Application Data

(63) Continuation-in-part of application No. 17/026,417, filed on Sep. 21, 2020, now Pat. No. 11,793,896.

(60) Provisional application No. 63/134,605, filed on Jan. 7, 2021, provisional application No. 63/054,985, filed on Jul. 22, 2020.

(51) Int. Cl.
*A61L 2/10* (2006.01)
*A61L 2/26* (2006.01)
*F21V 29/503* (2015.01)

(52) U.S. Cl.
CPC ...... *A61L 2/10* (2013.01); *A61L 2/26* (2013.01); *F21V 29/503* (2015.01); *A61L 2202/11* (2013.01)

(58) Field of Classification Search
CPC ............ A61L 2/10; A61L 2/26; F21V 29/503
See application file for complete search history.

(56) References Cited

U.S. PATENT DOCUMENTS 6,630,105 B1 * 10/2003 O'Neill .................. A61L 2/202
95/47

FOREIGN PATENT DOCUMENTS

| CN | 107575849 | 1/2018 |
|---|---|---|
| CN | 111 920 977 | 11/2020 |
| ES | 1 253 374 | 10/2020 |

OTHER PUBLICATIONS

English translation of CN 107575849 (Year: 2018).*
Communication re EP 21216489.1-1101, dated Mar. 15, 2023.
Extended European Search Report for EP App. No. 21216489.1-1101, dated May 20, 2022.

* cited by examiner

*Primary Examiner* — Sean E Conley
(74) *Attorney, Agent, or Firm* — Joseph M. Butscher; The Small Patent Law Group LLC

(57) ABSTRACT

A sanitizing system and method include a sanitizing head including an ultraviolet (UV) lamp, and a cooling manifold configured to deliver air to the UV lamp. The sanitizing system can also include an exhaust sub-system.

20 Claims, 20 Drawing Sheets

SYSTEMS AND METHODS FOR COOLING ULTRAVIOLET (UV) LAMPS

RELATED APPLICATIONS

This application is a continuation-in-part of U.S. patent application Ser. No. 17/026,417, entitled "Portable Sanitizing Systems and Methods," filed Sep. 21, 2020, which is hereby incorporated by reference in its entirety.

U.S. patent application Ser. No. 17/026,417, in turn, relates to and claims priority benefits from U.S. Provisional Patent Application No. 63/054,985, entitled "Portable Sanitizing Systems and Methods," filed Jul. 22, 2020.

This Application also relates to and claims priority benefits from U.S. Provisional Patent Application No. 63/134,605, entitled "Systems and Methods for Cooling Ultraviolet (UV) Lamps," filed Jan. 7, 2021, which is hereby incorporated by reference in its entirety.

FIELD OF THE DISCLOSURE

Embodiments of the present disclosure generally relate to systems and methods for cooling ultraviolet (UV) light emitters of sanitizing systems, such as may be used to sanitize structures and areas within vehicles, such as commercial aircraft.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light. In order to sanitize a surface of a structure, a known UV light sterilization method emits a broad spectrum UVC light onto the structure.

During operation, UV light emitters typically are cooled. However, known fans may not uniformly cool the UV light emitters. As such, the UV light emitters may overheat. Further, such overheated UV light emitters may produce high ozone concentrations in a confined space.

SUMMARY OF THE DISCLOSURE

A need exists for a system and a method for effectively and efficiently cooling UV light emitters of a UV lamp. Further, a need exists for a system and a method for reducing ozone produced during operation of a UV lamp.

With those needs in mind, certain embodiments of the present disclosure provide a sanitizing system including a sanitizing head having an ultraviolet (UV) lamp, and a cooling manifold configured to deliver air to the UV lamp.

In at least one embodiment, the sanitizing system further includes a wand assembly. The wand assembly includes the sanitizing head. As an example, the sanitizing system further includes a backpack assembly coupled to the wand assembly. As another example, the sanitizing system further includes a case assembly coupled to the wand assembly.

In at least one embodiment, the sanitizing head is a fixture within an enclosed space.

As an example, the cooling manifold includes one or more air outlets configured to pass the air onto and around the UV lamp.

As an example, the sanitizing head includes a shroud. The cooling manifold is formed within the shroud.

In at least one embodiment, the sanitizing system further includes a port having a channel in fluid communication with the cooling manifold.

As an example, the cooling manifold includes a plenum, a connecting conduit that fluidly couples the plenum to the channel, an air delivery line in fluid communication with the plenum, and one or more air outlets in fluid communication with the air delivery line.

In at least one embodiment, the cooling manifold includes one or more directing slots defined by one or more arcuate fins, and one or more air outlets fluid coupled to the one or more directing slots.

In at least one embodiment, the sanitizing system also includes an exhaust sub-system. For example, the exhaust sub-system includes one or more exhaust ports formed in a shroud of the sanitizing head.

Certain embodiments of the present disclosure provide a sanitizing method including operating an ultraviolet (UV) lamp of a sanitizing head to emit UV light onto a component; and delivering air to the UV lamp by a cooling manifold.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

In at least one embodiment, a sanitizing system includes a UV lamp. The UV lamp can be part of a wand assembly, such as of a portable sanitizing system. The wand assembly can be coupled to a backpack assembly, a case assembly, a cart assembly, or the like. In at least one other embodiment, the wand assembly is not coupled to a backpack assembly, a case assembly, or a cart assembly. In at least one other embodiment, the UV lamp can be fixed in position. A cooling manifold is configured to allow air to blow across one or more UV light emitters (such as a bulb) of the UV lamp.

In at least one embodiment, the sanitizing system includes features for cooling electronics and one or more UV light emitters, such as a UV bulb. Further, the sanitizing system can also be configured to displace any generated ozone from the UV lamp, for example.

In at least one embodiment, the cooling manifold is configured to supply cool jetted air radially around a UV bulb. The UV lamp and cooling manifold can be part of a wand assembly. In at least one other embodiment, the UV lamp and the cooling manifold can be permanently fixed within an environment, such as within an internal cabin of a vehicle.

Figure 1:
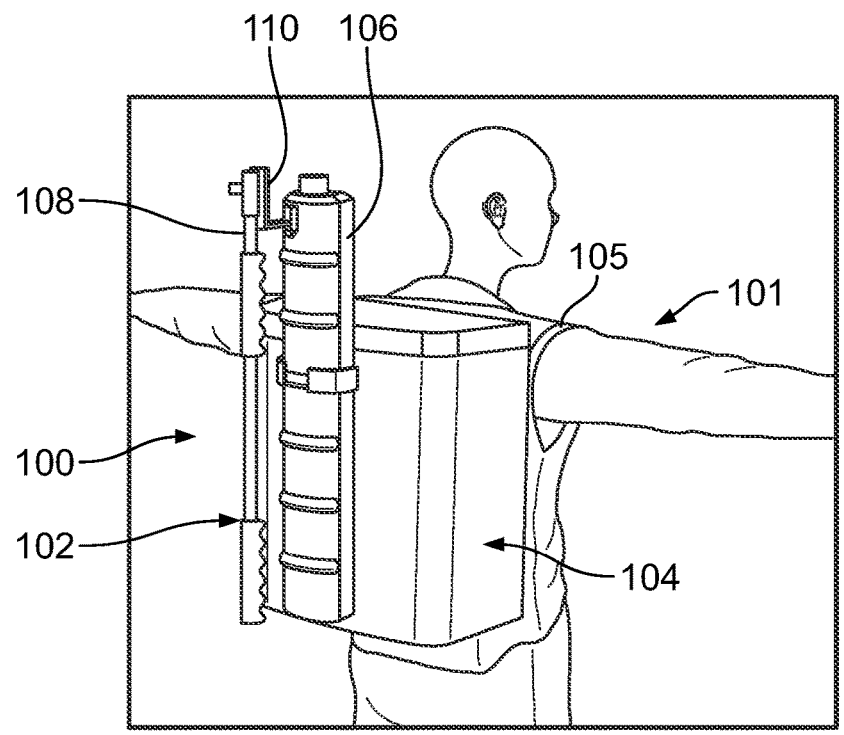
FIG. 1 illustrates a perspective view of a portable sanitizing system worn by an individual, according to an embodiment of the present disclosure.

FIG. 1 illustrates a perspective view of a portable sanitizing system 100 worn by an individual 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

In at least one other embodiment, the portable sanitizing system 100 may not be worn by the individual 101. For example, the portable sanitizing system 100 may include a case assembly that is configured to be opened and closed. The case assembly may store the wand assembly 102 when not in use. The case assembly may be opened to allow the wand assembly 102 to be removed and operated. In at least one other embodiment, the portable sanitizing system 100 may include a moveable cart assembly.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

In at least one other embodiment, the wand assembly 102 is stored within a case assembly in a stowed position. For example, the wand assembly 102 in the stowed position is contained within a closed case assembly. The case assembly may be opened to allow the wand assembly 102 to be removed and deployed.

Figure 2:
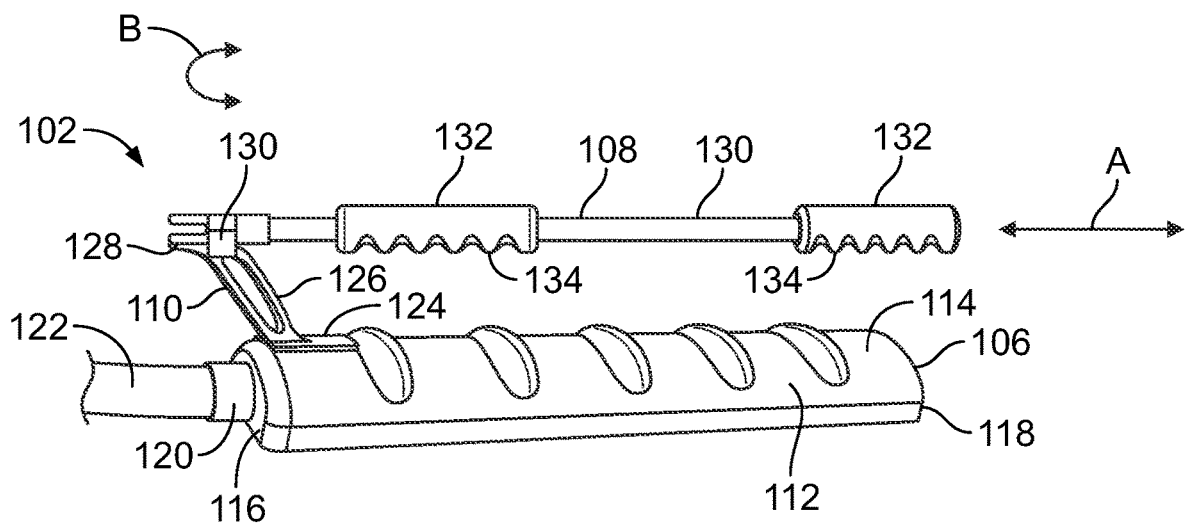
FIG. 2 illustrates a perspective lateral top view of a wand assembly, according to an embodiment of the present disclosure.

FIG. 2 illustrates a perspective lateral top view of the wand assembly 102, according to an embodiment of the present disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp.

Optionally, the wand assembly 102 may include the sanitizing head 106 connected to a fixed handle. Further, the wand assembly 102 may be sized and shaped differently than shown.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, the electrical cords, cables, wiring, or the like may be outside of the hose 122. In at least one embodiment, the hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 may include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 may include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 may be fixed to the coupler 110).

In at least one other embodiment, the wand assembly 102 does not include the coupler 110. Instead, the handle 108 may be fixed to the shroud 112, for example.

In at least one embodiment, the handle 108 includes a rod, pole, beam, or the like 130, which may be longer than the shroud 112. Optionally, the rod 130 may be shorter than the shroud 112. One or more grips 132 are secured to the rod 130. The grips 132 are configured to be grasped and held by an individual. The grips 132 may include ergonomic tactile features 134.

Optionally, the wand assembly 102 can be sized and shaped differently than shown. For example, in at least one example, the handle 108 can be fixed in relation to the shroud 112. Further, the handle 108 may not be configured to move relative to itself and/or the shroud 112. For example, the handle 108 and the shroud 112 can be integrally molded and formed as a single unit.

Figure 3:
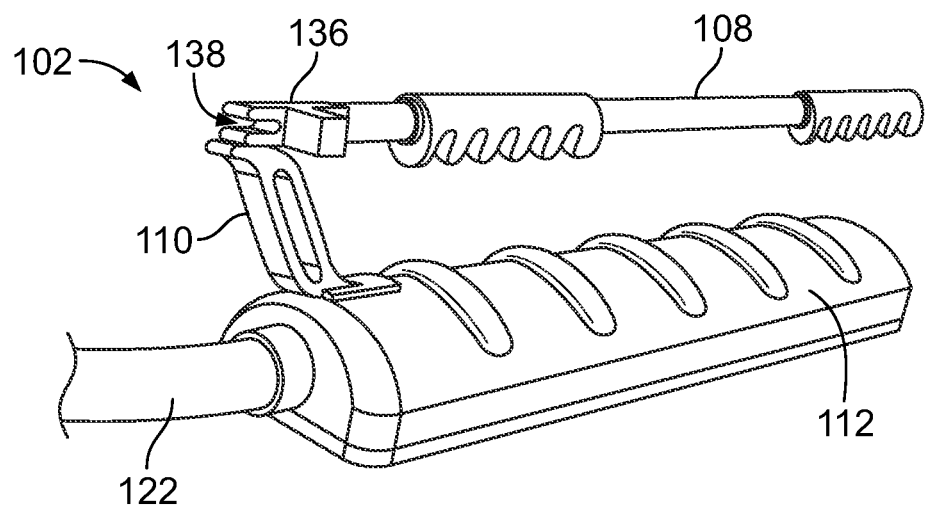
FIG. 3 illustrates a perspective rear view of the wand assembly of FIG. 2.
Figure 4:
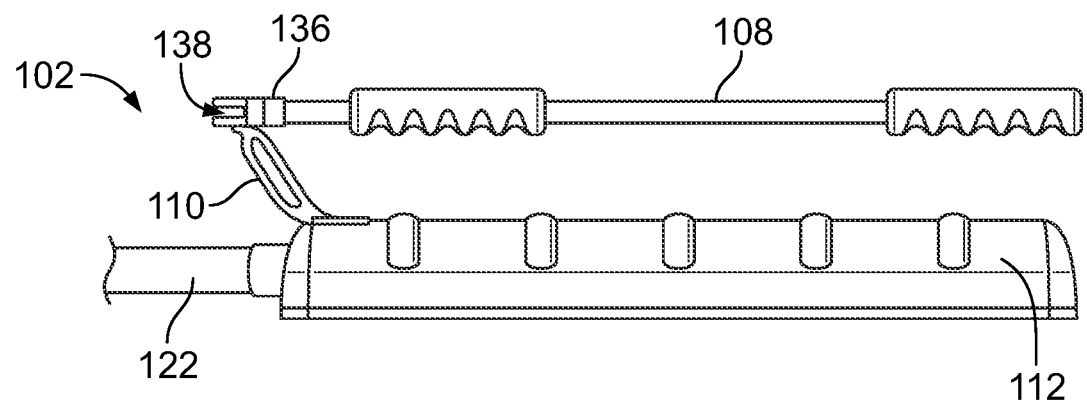
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 may pivotally couple to the coupler 110 through a bearing 136 having a pivot axle 138 that pivotally couples the handle 108 to the coupler 110. The handle 108 may further be configured to linearly translate into and out of the bearing 136. For example, the handle 108 may be configured to telescope in and out. Optionally, or alternatively, in at least one embodiment, the handle 108 may include a telescoping body that allows the handle 108 to outwardly extend and inwardly recede. In at least one other embodiment, the handle 108 may not be configured to move, extend, retract, or the like relative to the shroud 112.

Figure 5:
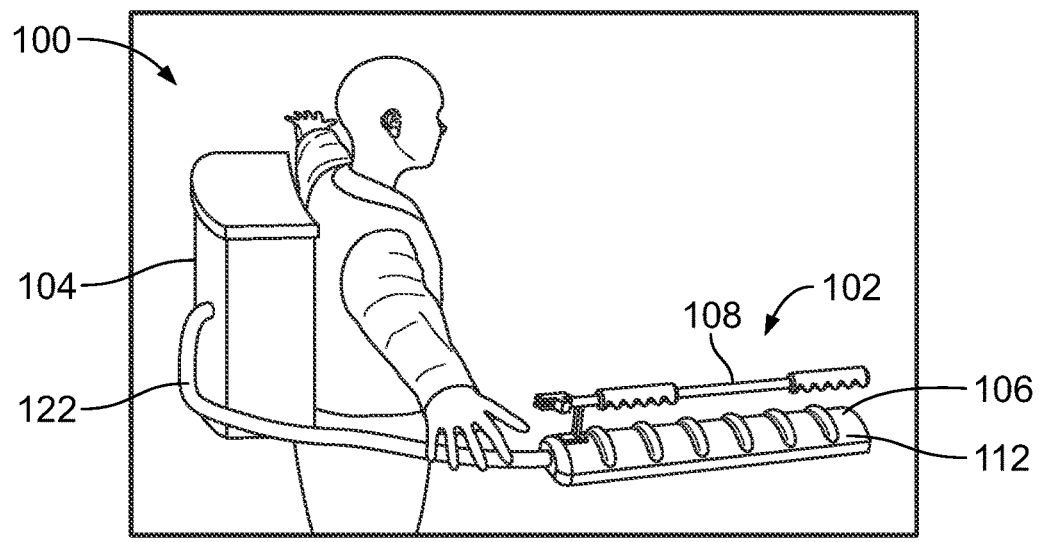
FIG. 5 illustrates a perspective view of the portable sanitizing system in a compact deployed position, according to an embodiment of the present disclosure.

FIG. 5 illustrates a perspective view of the portable sanitizing system 100 in a compact deployed position, according to an embodiment of the present disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
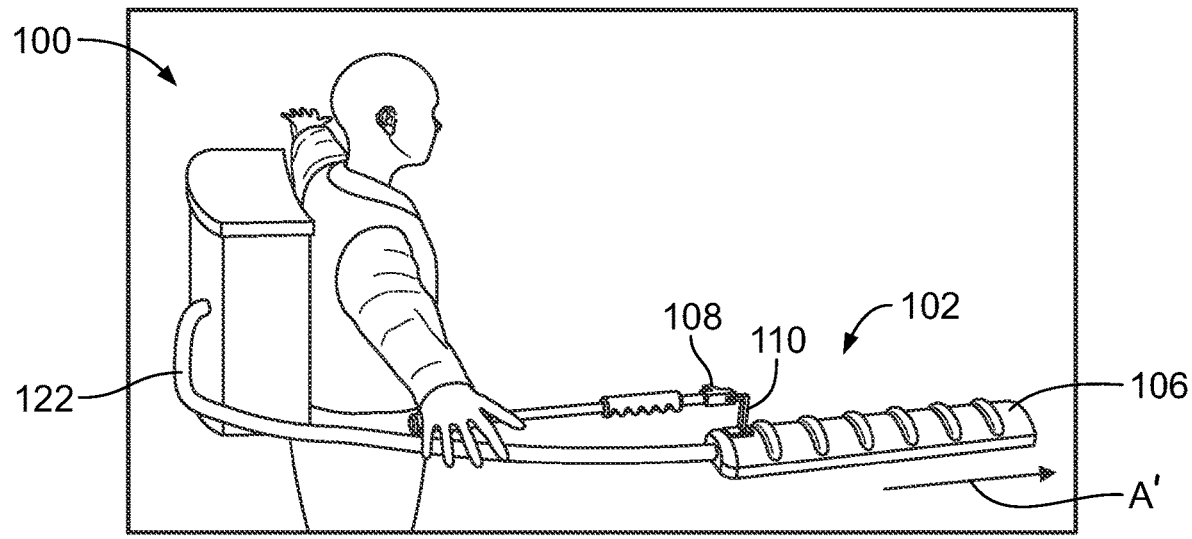
FIG. 6 illustrates a perspective view of the portable sanitizing system having a sanitizing head in an extended position, according to an embodiment of the present disclosure.

FIG. 6 illustrates a perspective view of the portable sanitizing system 100 having the sanitizing head 106 in an extended position, according to an embodiment of the present disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
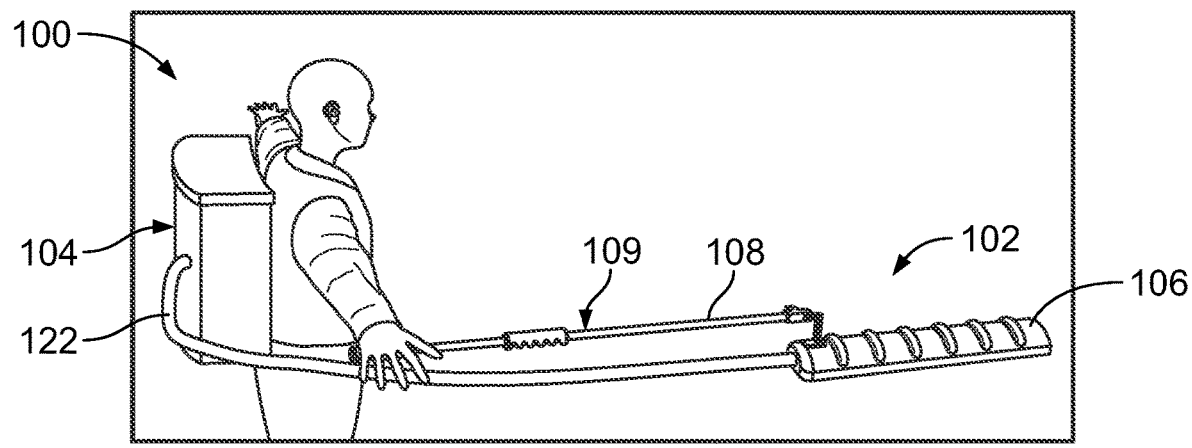
FIG. 7 illustrates a perspective view of the portable sanitizing system having the sanitizing head in an extended position and a handle in an extended position, according to an embodiment of the present disclosure.

FIG. 7 illustrates a perspective view of the portable sanitizing system 100 having the sanitizing head 106 in an extended position and the handle 108 in an extended position, according to an embodiment of the present disclosure. To reach even further, the handle 108 may be configured to linearly translate, such as through a telescoping portion, to allow the sanitizing head 106 to reach further outwardly. Alternatively, the handle 108 may not be configured to extend and retract.

In at least one embodiment, the handle 108 may include a lock 109. The lock 109 is configured to be selectively operated to secure the handle 108 into a desired extended (or retracted) position.

Figure 8:
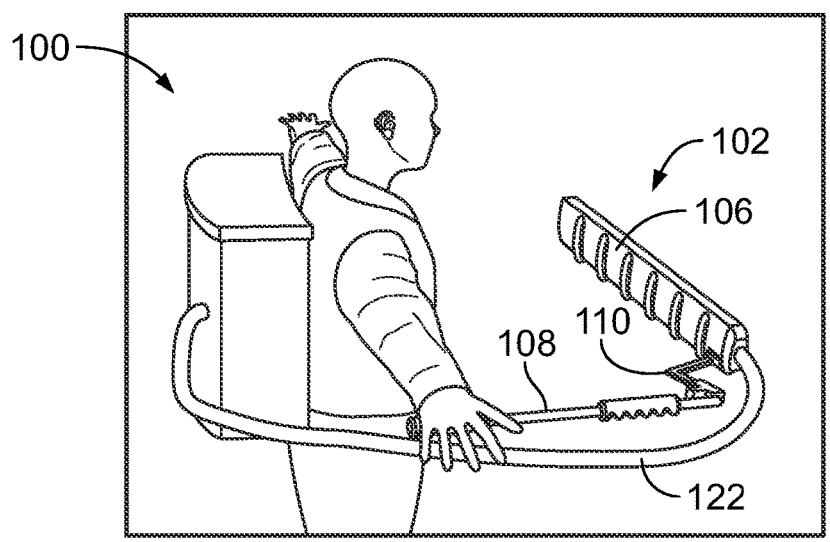
FIG. 8 illustrates a perspective view of the portable sanitizing system having the sanitizing head rotated in relation to the handle, according to an embodiment of the present disclosure.

FIG. 8 illustrates a perspective view of the portable sanitizing system 100 having the sanitizing head 106 rotated in relation to the handle 108, according to an embodiment of the present disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108.

Figure 9:
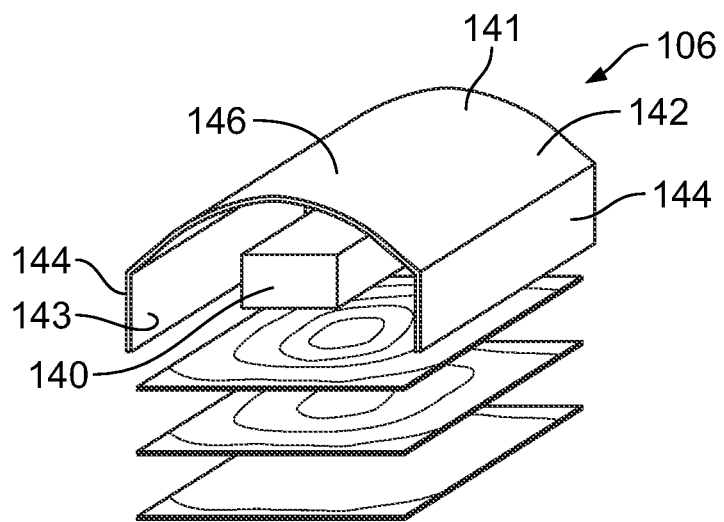
FIG. 9 illustrates a perspective end view of a UV lamp and a reflector of the sanitizing head, according to an embodiment of the present disclosure.

FIG. 9 illustrates a perspective end view of a UV lamp 140 and a reflector 142 of the sanitizing head 106, according to an embodiment of the present disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 may be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 may be or include a shell formed of fiberglass, and the reflector 142 may be formed of Teflon that provides a 98% reflectivity. In at least one embodiment, the reflector 142 may be a multi-piece reflector.

The reflector 142 may extend along an entire length of the underside 141 of the shroud 112. Optionally, the reflector 142 may extend along less than an entire length of the underside 141 of the shroud 112.

The UV lamp 140 may extend along an entire length (or along substantially the entire length, such as between the ends 116 and 118). The UV lamp 140 is secured to the reflector 142 and/or the shroud 112 through one or more mounts, such as brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 may be or include a 300 W bulb that is configured to emit UV light having a wavelength of 222 nm. Optionally, the UV lamp 140 may be configured to emit UV light in other portions of the UV spectrum, such as the UVC spectrum. For example, the UV lamp 140 may be configured to emit UV light having a wavelength of 254 nm. In at least one other embodiment, the UV lamp 140 may be configured to emit UV light in portions of the UV spectrum other than the far UV spectrum, or the UVC spectrum.

As shown, the reflector 142 includes flat, upright side walls 144 connected together through an upper curved wall 146. The upper curved wall 146 may be bowed outwardly away from the UV lamp 140. For example, the upper curved wall 146 may have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
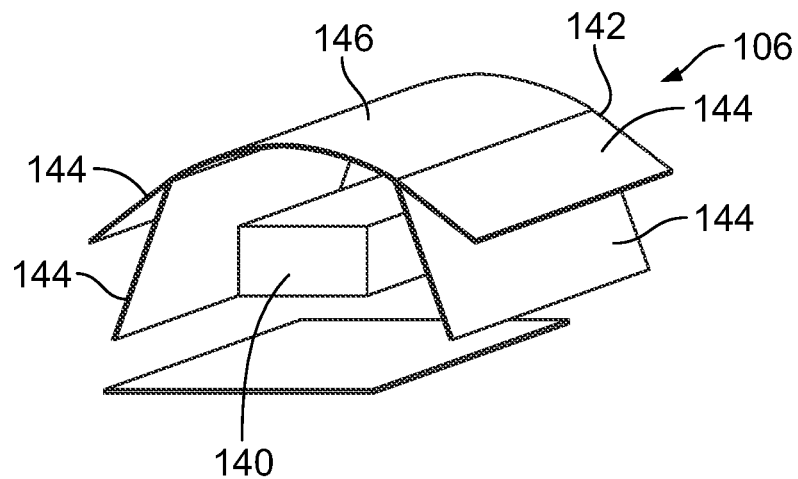
FIG. 10 illustrates a perspective end view of a UV lamp and a reflector of the sanitizing head, according to an embodiment of the present disclosure.

FIG. 10 illustrates a perspective end view of the UV lamp 140 and a reflector 142 of the sanitizing head, according to an embodiment of the present disclosure. The reflector 142 shown in FIG. 10 is similar to the reflector 142 shown in FIG. 9, except that the side walls 144 may outwardly cant from the upper curved wall 146.

Figure 11:
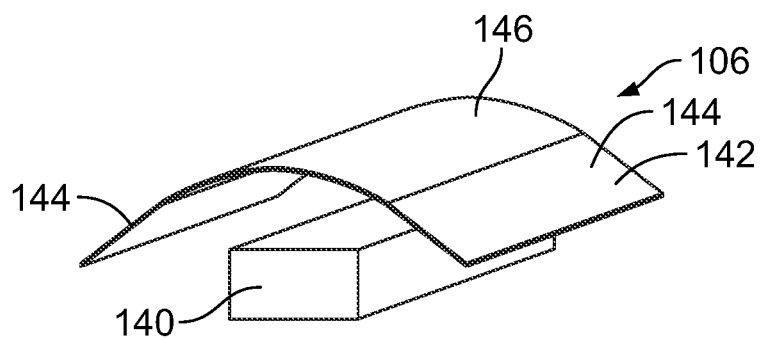
FIG. 11 illustrates a perspective end view of a UV lamp and a reflector of the sanitizing head, according to an embodiment of the present disclosure.

FIG. 11 illustrates a perspective end view of the UV lamp 140 and the reflector 142 of the sanitizing head, according to an embodiment of the present disclosure. In this embodiment, the side walls 144 may be curved according to the curvature of the upper curved wall 146.

Figure 12:
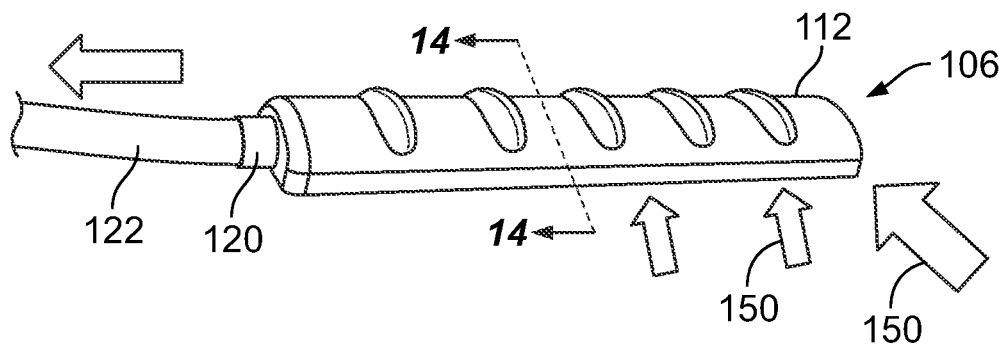
FIG. 12 illustrates a perspective top view of the sanitizing head.
Figure 13:
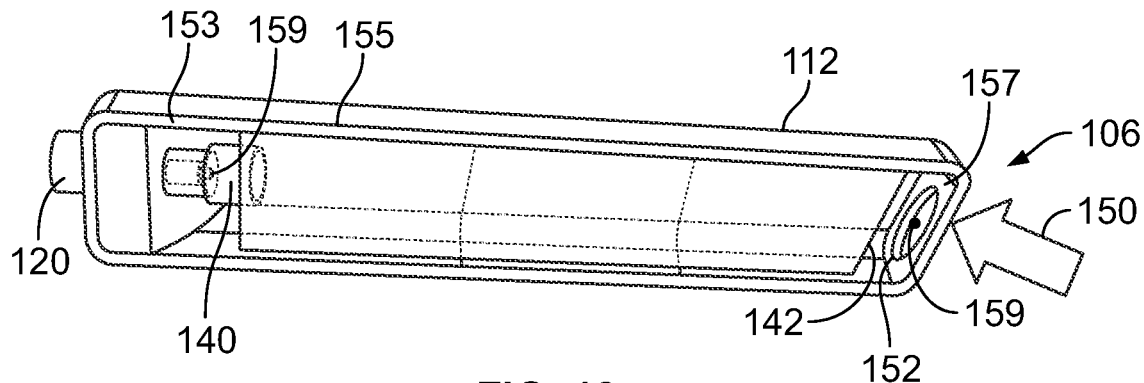
FIG. 13 illustrates a perspective bottom view of the sanitizing head.
Figure 14:
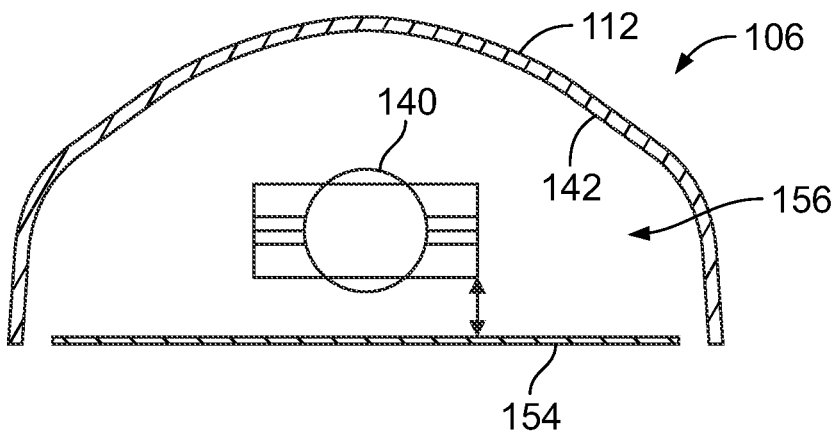
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104.

In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIG. 13, in particular, a bumper 153 may be secured to an exposed lower circumferential edge 155 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 may be spaced around the lower surface of the shroud 112 such that they do not provide a direct view of the UV lamp 140. For example, the openings 152 may be positioned underneath portions that are spaced apart from the UV lamp 140.

Referring to FIG. 14, in particular, the sanitizing head 106 may include a cover plate 154 below the UV lamp 140. The cover plate 154 may be formed of glass, for example, and may be configured to filter UV light emitted by the UV lamp 140. The UV lamp 140 may be secured within an interior chamber 156 defined between the reflector 142 and the cover plate 154. In at least one embodiment, the cover plate 154 is or otherwise includes a far UV band pass filter. For example, the cover plate 154 may be a 222 nm band pass filter that filters UV light emitted by the UV lamp 140 to a 222 nm wavelength. As such, UV light that is emitted from the sanitizing head 106 may be emitted at a wavelength of 222 nm. As another example, the cover plate 154 may be a 254 nm band filter that filters UV light emitted by the UV lamp 140 to a 254 nm wavelength.

Referring to FIGS. 13 and 14, a rim 157 (such as a 0.020" thick Titanium rim) may connect the cover plate 154 to the shroud 112. The rim 157 may distribute impact loads therethrough and/or therearound.

In at least one embodiment, ranging light emitting diodes (LEDs) 159 may be disposed proximate to ends of the UV lamp 140. The ranging LEDs 159 may be used to determine a desired range to a structure that is to be sanitized, for example. In at least one embodiment, the ranging LEDs 159 may be disposed on or within the rim 157 and/or the cover plate 154. As another example, the sanitizing head 106 may be configured for range guidance, as disclosed in U.S. Provisional Application No. 63/027,869, which was filed May 20, 2020.

Figure 15:
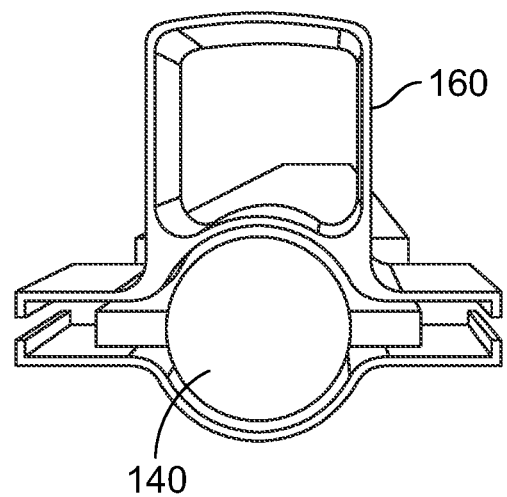
FIG. 15 illustrates a perspective end view of the UV lamp secured to a mounting bracket, according to an embodiment of the present disclosure.

FIG. 15 illustrates a perspective end view of the UV lamp 140 secured to a mounting bracket or clamp 160, according to an embodiment of the present disclosure. Each end of the UV lamp 140 may be coupled to mounting bracket or clamp 160, which secures the UV lamp 140 to the shroud 112 (shown in FIGS. 12-14). A buffer, such as a thin (for example, 0.040") sheet of silicon may be disposed between the end of the UV lamp 140 and the bracket 160. Optionally, the UV lamp 140 may be secured to the shroud 112 through brackets or clamps that differ in size and shape than shown. As another example, the UV lamp 140 may be secured to the shroud 112 through adhesives, fasteners, and/or the like.

Figure 16:
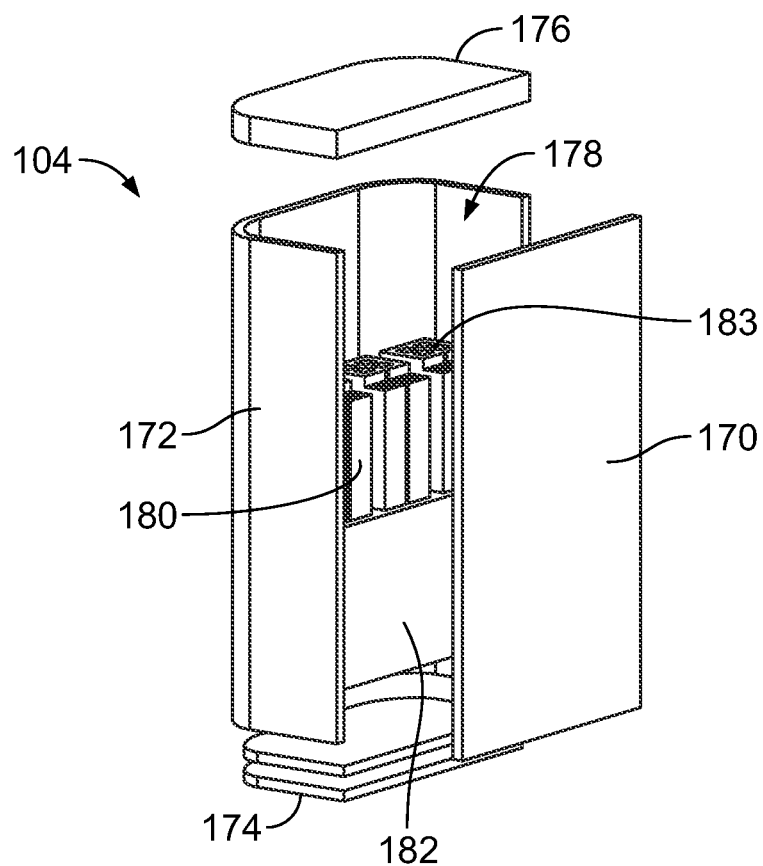
FIG. 16 illustrates a perspective exploded view of a backpack assembly, according to an embodiment of the present disclosure.

FIG. 16 illustrates a perspective exploded view of the backpack assembly 104, according to an embodiment of the present disclosure. The backpack assembly 104 includes a front wall 170 that couples to a rear shell 172, a base 174, and a top cap 176. An internal chamber 178 is defined between the front wall 170, the rear shell 172, the base 174, and the top cap 176. One or more batteries 180, such as rechargeable Lithium batteries, are contained within the internal chamber 178. An air generation sub-system 182 is also contained within the internal chamber 178. The air generation sub-system 182 is in fluid communication with an air tube within the hose 122 (shown in FIG. 2, for example). The air generation sub-system 182 may include an airflow device, such as a vacuum generator, an air blower, and/or the like. The airflow device is configured to generate airflow to cool the UV lamp, draw air from the sanitizing head 106 into the backpack assembly 104 and out through an exhaust, draw or otherwise remove generated ozone away from the shroud 112, and/or the like.

One or more air filters 183, such as carbon filters, are within the backpack assembly 104. The air filters 183 are in communication with the air tube or other such delivery duct or line that routes air through the hose 122 and into the backpack assembly 104. The air filters 183 are configured to filter the air that is drawn into the backpack assembly 104 from the shroud 112. For example, the air filters 183 may be configured to remove, deactivate, or otherwise neutralize ozone.

The batteries 180 and/or a power supply within the backpack assembly 104 provides operating power for the UV lamp 140 of the sanitizing head 106 (shown in FIG. 2, for example). The top wall 176 may be removably coupled to the front wall 170 and the rear shell 172. The top wall 176 may be removed to provide access to the batteries 180 (such as to remove and/or recharge the batteries), for example. Additional space may be provided within the backpack assembly 104 for storage of supplies, additional batteries, additional components, and/or the like. In at least one embodiment, the front wall 170, the rear shell 172, the base 174, and the top cap 176 may be formed of fiberglass epoxy.

Figure 17:
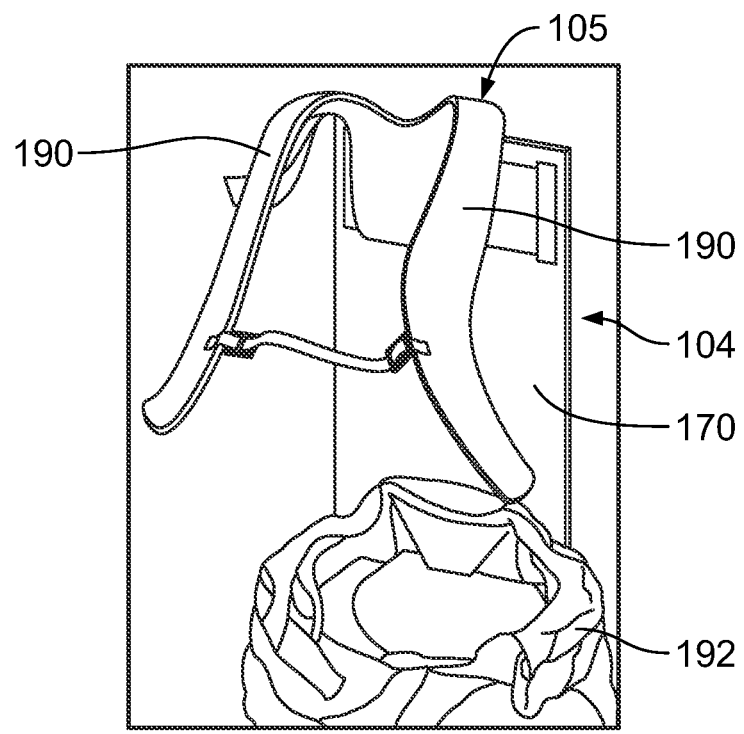
FIG. 17 illustrates a perspective front view of a harness coupled to a backpack assembly, according to an embodiment of the present disclosure.

FIG. 17 illustrates a perspective front view of the harness 105 coupled to the backpack assembly 104, according to an embodiment of the present disclosure. The harness 105 may include shoulder straps 190 and/or a waist or hip belt or strap 192, which allow the individual to comfortably wear the backpack assembly 104.

Referring to FIGS. 1-17, in operation, the individual may walk through an area wearing the backpack assembly 104. When a structure to be sanitized is found, the individual may position grasp the handle 108 and position the sanitizing head 106 as desired, such as by extending and/or rotating the sanitizing head 106 relative to the handle 108. The individual may then engage an activation button on the handle 108, for example, to activate the UV lamp 140 to emit sanitizing UV light onto the structure. As the UV lamp 140 is activated, air 150 is drawn into the shroud 112 to cool the UV lamp 140, and divert any generated ozone into the backpack assembly 104, where it is filtered by the air filters 183.

The extendable wand assembly 102 allows the sanitizing head 106 to reach distant areas, such as over an entire set of three passenger seats, from a row within an internal cabin of a commercial aircraft.

Figure 18:
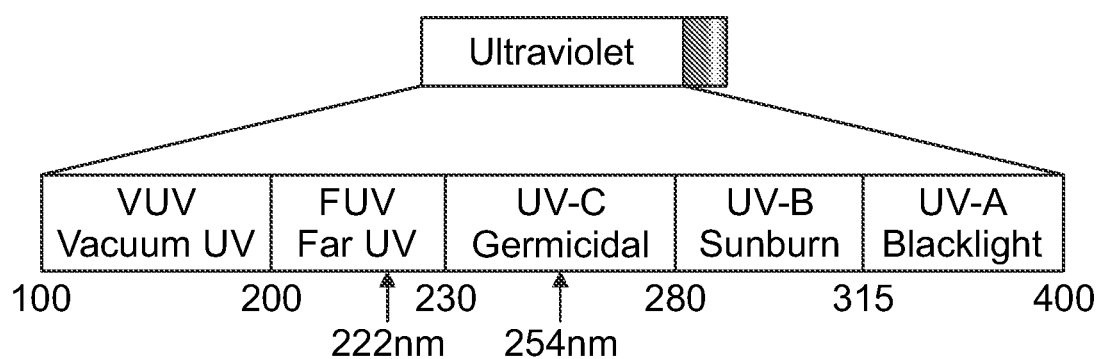
FIG. 18 illustrates an ultraviolet light spectrum.

FIG. 18 illustrates an ultraviolet light spectrum. Referring to FIGS. 1-18, in at least one embodiment, the sanitizing head 106 is configured to emit sanitizing UV light (through operation of the UV lamp 140) within a far UV spectrum, such as between 200 nm to 230 nm. In at least one embodiment, the sanitizing head 106 emits sanitizing UV light having a wavelength of 222 nm. In at least one other embodiment, the sanitizing head 106 is configured to emit sanitizing UV light within the UVC spectrum, such as between 230 nm to 280 nm. For example, the sanitizing head 106 emits sanitizing UV light having a wavelength of 254 nm. In at least one other embodiment, the sanitizing head 106 is configured to emit sanitizing UV light within different portions of the UV spectrum.

Figure 19:
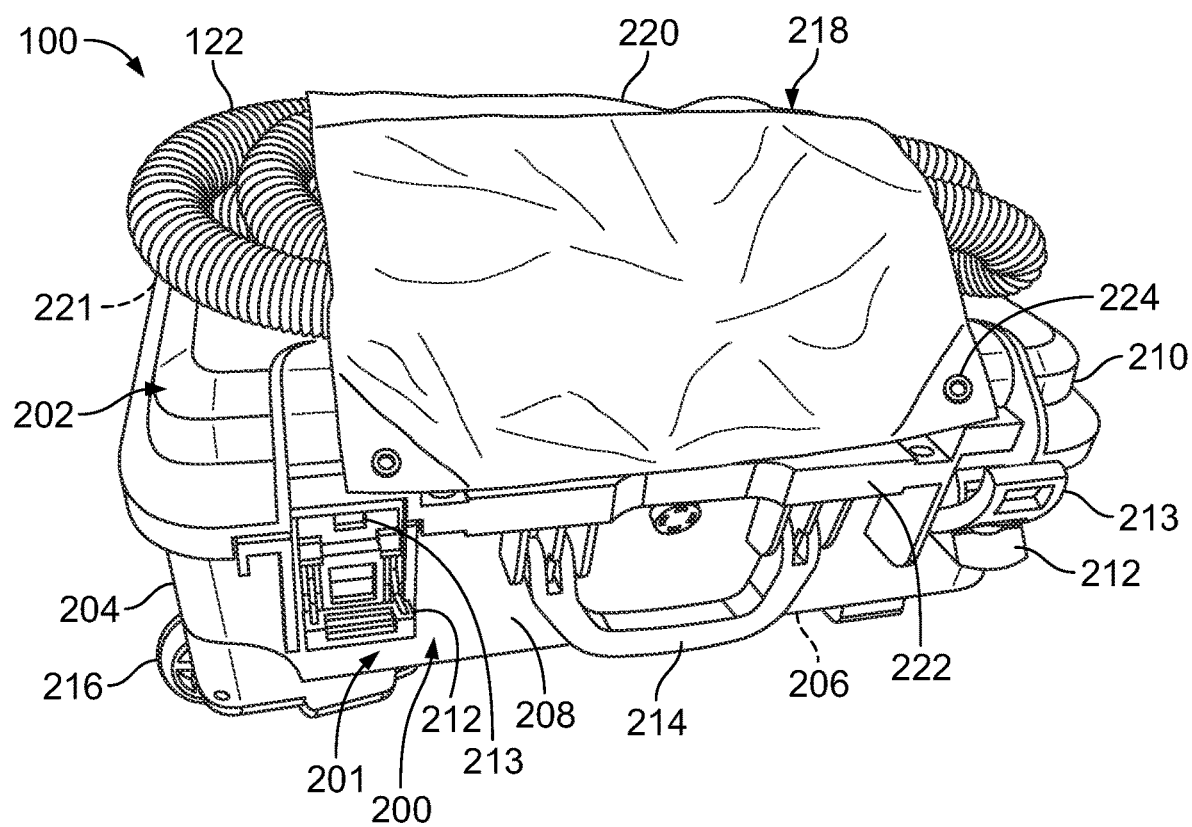
FIG. 19 illustrates a perspective view of a portable sanitizing system, according to an embodiment of the present disclosure.

FIG. 19 illustrates a perspective view of a portable sanitizing system 100, according to an embodiment of the present disclosure. The portable sanitizing system 100 includes a case assembly 200 that is configured to store the wand assembly 102 (hidden from view in FIG. 19) when the case assembly 200 is in a closed position, as shown in FIG. 19.

The case assembly 200 may be formed of plastic, for example. The case assembly 200 includes a main body 201, such as a shell, lower body portion, or the like. A cover 202, such as a lid, or upper body portion, is moveably coupled to the main body 201. For example, the cover 202 may be coupled to the main body 201 through a hinge that allows the cover 202 to be opened and closed relative to the main body 201.

The main body 201 includes a base 204 connected to a rear wall 206, lateral walls 208, and a top wall 210. The cover 202 is moveably coupled to a first lateral wall 208, such as through a hinge. One or more latches 212 are disposed on a second lateral wall 208, opposite from the first lateral wall 208. The latches 212 are configured to engage one or more reciprocal latch members 213 extending from the cover 202 to secure the cover 202 in the closed position. The latches 212 may be engaged by an individual to disengage the latch members 213 to allow the cover 202 to be pivoted into an open position.

A handle 214 is secured to the case assembly 200. For example, the handle 214 is pivotally secured to a lateral wall 208. The handle 214 is configured to be grasped by an individual so that the portable sanitizing system 100 may be carried. Optionally, the handle 214 may be secured to other portions of the case assembly 200, such as the top wall 210. In at least one embodiment, the handle 214 may be configured to retract into the case assembly 200 into a fully retracted position, and extend out of (for example, telescope out of) the case assembly 200 into a fully extended position.

Casters 216 or other such wheels may be rotatably secured to a portion of the case assembly 200. For example, two casters 216 may be rotatably secured to the base 204 proximate to the rear wall 206. An individual may tilt the case assembly 200 so that the casters 216 contact a floor. In this manner, the individual may roll the portable sanitizing system 100 via the casters 216 (and optionally through a handle in an extended position from the top wall 210). Alternatively, the case assembly 200 may not include the casters 216.

The hose 122 may outwardly extend from the case assembly 200. In the closed position, when the wand assembly 102 is in a stowed position within the case assembly 200, the hose 122 may be coiled over the cover 202. A hose retainer 218 may secure the hose 122 in place on the cover 202. For example, the hose retainer 218 may include a flexible fabric sheet 220 that is secured to a first side 221 of the cover 202, and may removably secured to an opposite second side 222 of the cover 202, such as through one or more fastening members 224, such as hooks and loops, latches, clips, and/or the like. The hose retainer 218 is configured to secure the hose 122 on the cover 202 when the wand assembly 102 is within a storage chamber of the case assembly 200 and the cover 202 is in a closed position. Alternatively, the hose 122 may be contained within a storage chamber of the case assembly 200 when the wand assembly 102 is not in use. That is, the storage chamber may be sized and shaped to also contain the hose 122 when the wand assembly 102 is also within the storage chamber and the cover 202 is in the closed position.

The wand assembly 102 within the case assembly 200 in the closed position is protected from inadvertent engagement, bumping, and the like. That is, by storing the wand assembly 102 within the case assembly 200, which is closed, when the wand assembly 102 is not in use, the portable sanitizing system 100 protects the wand assembly 102 from potential damage, and increases the useful life of the wand assembly 102.

Figure 20:
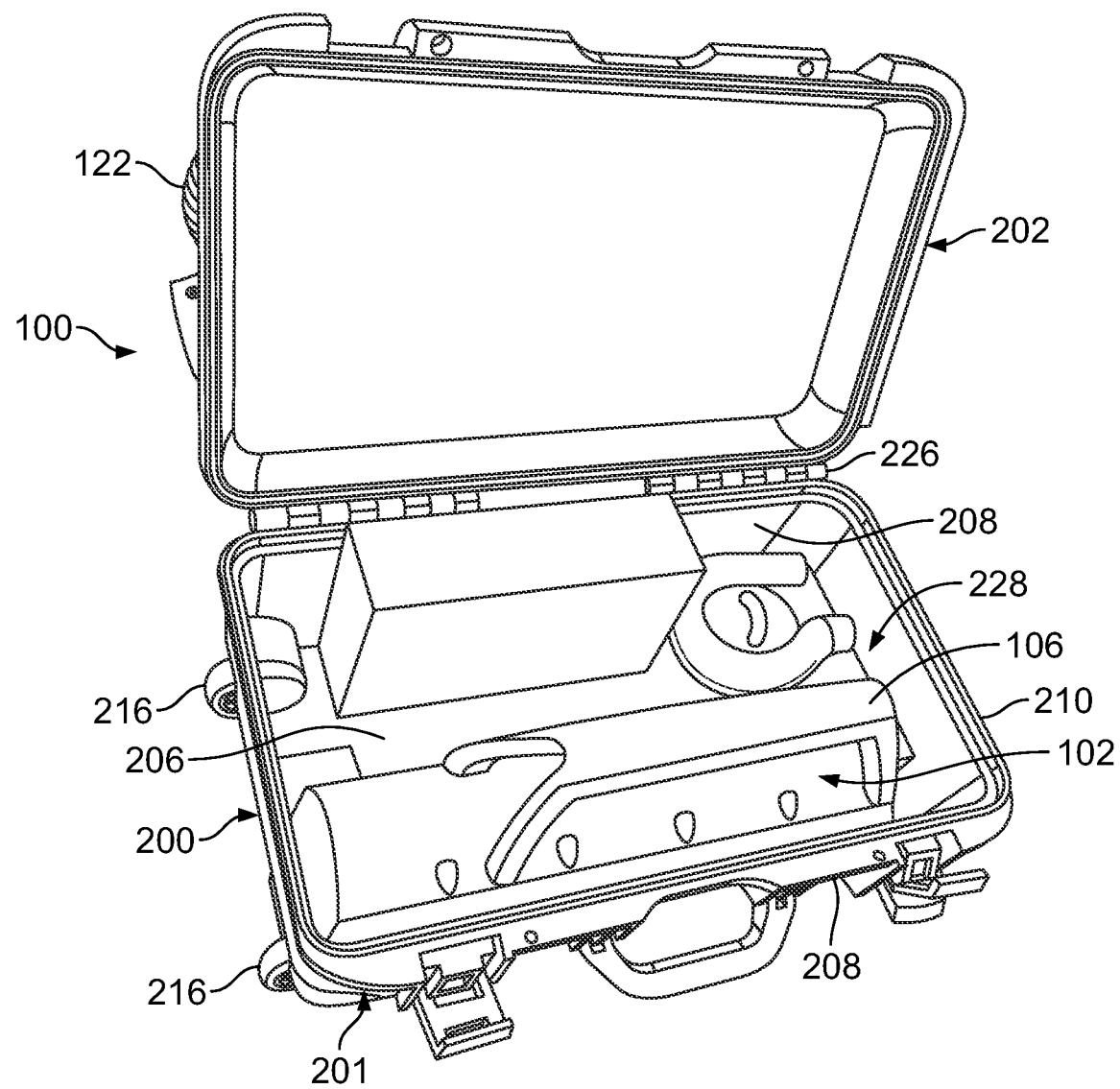
FIG. 20 illustrates a perspective view of the portable sanitizing system having a case assembly in an open position, according to an embodiment of the present disclosure.

FIG. 20 illustrates a perspective view of the portable sanitizing system 100 having the case assembly 200 in an open position, according to an embodiment of the present disclosure. As shown, the cover 202 is opened via a hinge 226 that pivotally couples the cover 202 to the main body 201.

An internal or storage chamber 228 is defined between the base 204, the lateral walls 208, the rear wall 206, and the top wall 210 (and the cover 202, when closed). Various components of the portable sanitizing system 100 may be stored within the storage chamber 228. For example, the components within the backpack assembly 104, as described with respect to FIG. 16, may be contained within the storage chamber 228.

For example, when not in use, the wand assembly 102 is contained within the storage chamber 228. Additionally, one or more batteries, such as rechargeable Lithium batteries, may be contained within the storage chamber 228.

An air generation sub-system (such as a cooling fan) may also be contained within the storage chamber 228. The air generation sub-system may be in fluid communication with an air tube within the hose 122. The hose 122 may be removably connected to the air generation sub-system. In at least one embodiment, the hose 122 is configured to be coupled to and uncoupled from the wand assembly 102 and the air generation sub-system. That is, the hose 122 may be removably coupled to the wand assembly 102 and the air generation sub-system.

One or more air filters, such as carbon filters, may also be within the storage chamber 228. The air filters may be in communication with the air tube or other such delivery duct or line that routes air through the hose 122.

Figure 21:
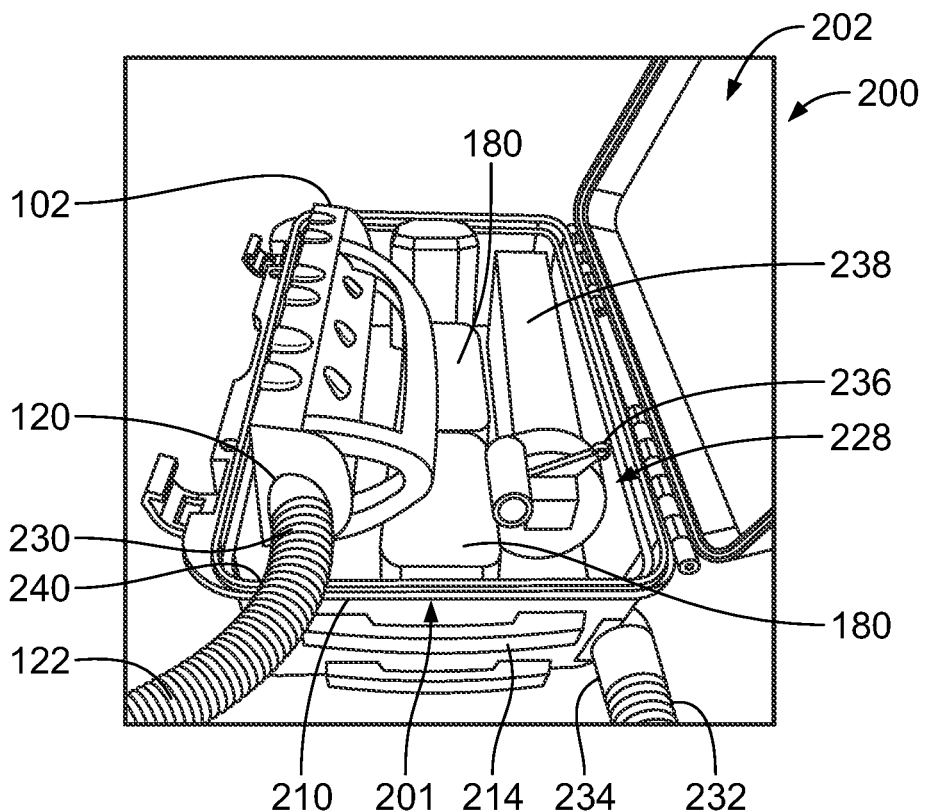
FIG. 21 illustrates a perspective view of the portable sanitizing system having the case assembly in the open position, according to an embodiment of the present disclosure.

FIG. 21 illustrates a perspective view of the portable sanitizing system 100 having the case assembly 200 in the open position, according to an embodiment of the present disclosure. The wand assembly 102 is configured to be stowed in the storage chamber 228. When the wand assembly 102 is to be used, the cover 202 is opened, and a first end 230 of the hose 122 is coupled to the port 120 of the wand assembly 102. In at least one embodiment, the hose 122 is configured to channel cooling air into the wand assembly 102, in order to cool the UV lamp 140 during activation.

A second end 232 of the hose 122 may be connected to a port 234 extending into and through a portion of the main body 201, such as through a portion of the top wall 210. The port 234 connects the hose 122 to an air generation sub-system, such as a cooling fan 236 that is within the storage chamber 228. The cooling fan 236 may be activated to generate cooling air that is delivered to the wand assembly 102 through the hose 122 (such as an air tube within the hose 122, or through an internal passage of the hose 122 itself).

One or more batteries 180 may also be stowed within the storage chamber 228. For example, three batteries 180 may be within the storage chamber 228.

A power supply 238 is also contained within the storage chamber 228. The power supply 238 may be coupled to the wand assembly 102 through a power cord (such as via a plug and receptacle fitting) to provide power to the wand assembly 102. Further, the power supply 238 may be configured to provide power to the batteries 180 (such as to recharge the batteries 180). The batteries 180 may be secured to the wand assembly 102 and provide power to the wand assembly 102, so that the wand assembly 102 may be used without connection to the power supply 238.

The cooling fan 236 couples to the hose 122 via the port 234. The cooling fan 236 may also include a diverter port that couples to an internal portion of the power supply 238. In this manner, cooling air may be delivered to both the hose 122 (and therefore the wand assembly 102), and the power supply 238, thereby providing cooling to both the wand assembly 102 and the power supply 238.

A hole 240 may be formed through a portion of the case assembly 200. For example, a hole 240 may be formed through a portion of the top wall 210 and sized and shaped to allow the hose 122 to pass therethrough. In this manner, the hose 122 may remain connected to the wand assembly 102 even when the wand assembly 102 is contained within the storage chamber 228 and the cover 202 is closed. Other portions of the hose 122 between the first end 230 and the second end 232 may be secured to the cover 202 by the hose retainer 218, as shown and described with respect to FIG. 19.

As shown, the handle 214 may be secured to the top wall 210 of the main body 201. The handle 214 may be configured to retracted into and extend out of the main body 201. For example, the handle 214 may be a telescoping handle.

The wand assembly 102 is removably secured within the storage chamber 228. For example, the wand assembly 102 may be removably secured within the storage chamber 228 by one or more latches, clips, or via an interference fit with a conforming portion of the case assembly 200.

The power supply 238 may be fixed in position within the storage chamber 228. For example, the power supply 238 may be fixed in the storage chamber 228 by one or more fasteners, adhesives, or the like. Optionally, the power supply 238 may be secured in position by one or more latches, clips, or the like.

The batteries 180 may similarly be fixed position within the storage chamber 228. For example, the batteries 180 may be fixed in the storage chamber 228 by one or more fasteners, adhesives, or the like. Optionally, the batteries 180 may be secured in position by one or more latches, clips, or the like. In at least one other embodiment, the batteries 180 may be removable, and configured to couple directly to the wand assembly 102 to provide power thereto.

Figure 22:
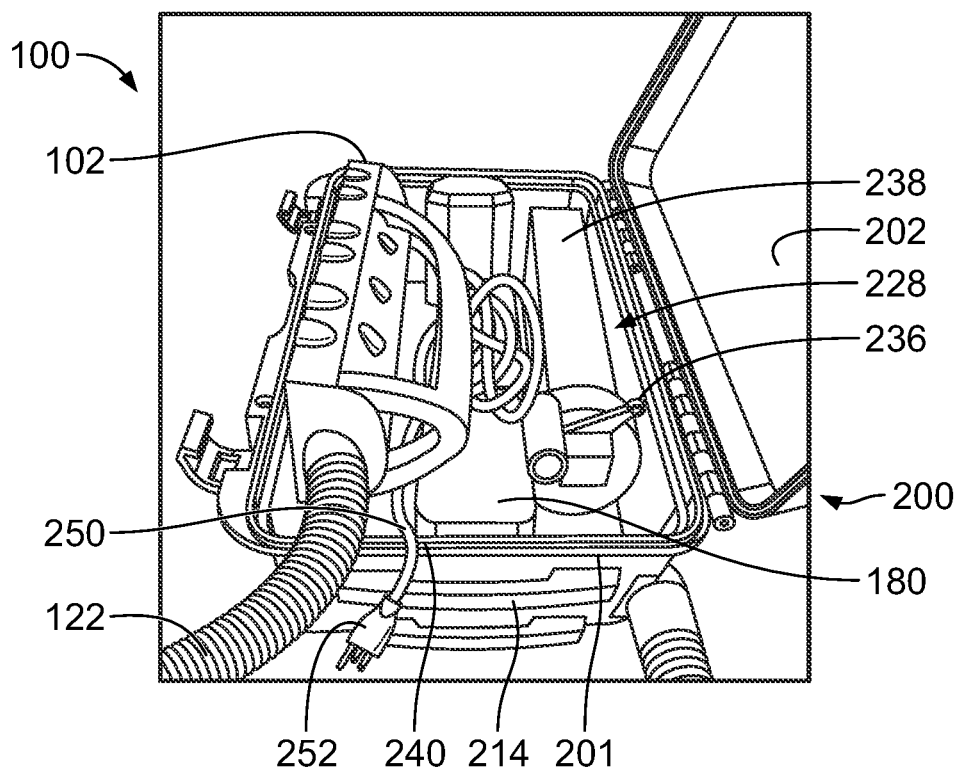
FIG. 22 illustrates a perspective view of the portable sanitizing system having the case assembly in the open position, according to an embodiment of the present disclosure.

FIG. 22 illustrates a perspective view of the portable sanitizing system 100 having the case assembly 200 in the open position, according to an embodiment of the present disclosure. A power cord 250 may also be stowed within the storage chamber 228. The power cord 250 is contained within the case assembly 200 when the cover 202 is closed and the portable sanitizing system 100 is moved when the wand assembly 102 is not being operated.

Optionally, the power cord 250 connects the power supply 238 to a source of power (such as a wall outlet). In addition to supply air to the wand assembly 102, the hose 122 also routes electrical cables and the like to the wand assembly 102 from the power supply 238 and the batteries 180.

Optionally, the hose 122 may not include electrical connections to the wand assembly 102. Instead, the wand assembly 102, the power cord 250 may plug into the wand assembly 102, via the plug 252, to supply power from the power supply 238 and/or the batteries 180. In this embodiment, as the wand assembly 102 is operated, the plug 252 of the power cord 250 is connected to a reciprocal receptacle of the wand assembly 102. An opposite end of the power cord 250 is connected to the power supply 238 (and/or, a battery 180). The power cord 250 extends out of the case assembly 200 through the hole 240. Thus, the wand assembly 102 may be removed from the storage chamber 228 and connected to the hose 122 and the power cord 250, which extend through the hole 240. The cover 202 may then be closed, thereby securely retaining the power supply 238, the batteries 180, and the like within the storage chamber 228. The wand assembly 102 may then be activated, as it is powered via the power supply 238 or one or more of the batteries 180, and the closed case assembly 200 may be moved, such as via an individual grasping the handle 214 and rolling the case assembly 200 via the casters 216 (shown in FIGS. 19 and 20).

Further, the hole 240 also allows intake air to be drawn into the storage chamber 228, even when the cover 202 is closed over the main body 201. Accordingly, the cooling fan 236 is able to receive fresh air, even when the cover 202 is closed.

The power supply 238 may be configured to receive power from a standard power supply, such as a source of alternating current power. For example, the power supply 238 may connect to the source of alternating current power through a power cord. The power cord 250 connects to the wand assembly 102, and is configured to deliver power to the wand assembly 102 to operate the UV lamp 140 from power received from the power supply 238 and optionally the batteries 180. For example, when the power supply 238 is connected to a source of alternating current power, the wand assembly 102 is powered by the power supply 238. In the absence of such power, the wand assembly 102 may be powered by the batteries 180. For example, the wand assembly 102 receives power from the batteries 180 the power supply 238 is not plugged into a power outlet. If the power supply 238 is plugged into a power outlet, one or more relays in the power supply 238 switch over from the batteries 180 to alternating current power supply from the power outlet.

Figure 23:
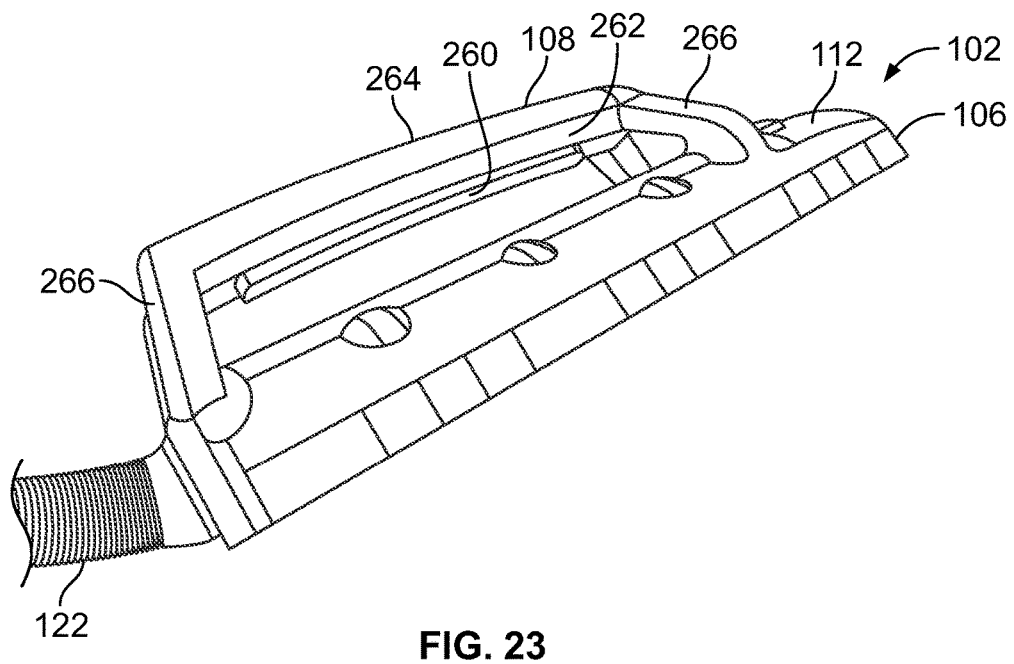
FIG. 23 illustrates a perspective lateral view of the wand assembly, according to an embodiment of the present disclosure.

FIG. 23 illustrates a perspective lateral view of the wand assembly 102, according to an embodiment of the present disclosure. As shown, the handle 108 may be fixed in relation to the shroud 112. For example, the handle 108 may be integrally molded and formed with the shroud 112. The wand assembly 102 may be small and compact in order to fit in confined spaced, such as within a flight deck of an aircraft.

An activation trigger 260 is moveably coupled to the handle 108. For example, the activation trigger 260 may be secured to an underside 262 of a main beam 264 of the handle 108. The activation trigger 260 is configured to be selectively pressed and/or depressed to activate and deactivate the UV lamp 140 of the wand assembly 102, as desired.

The activation trigger 260 may be located anywhere along the length of the handle 108. The activation trigger 260 may be shaped differently than shown. Further, the activation trigger 260 may be smaller or larger than shown. As an example, the activation trigger 260 may be a circular button, instead of an elongated bar or beam, as shown. Also, optionally, the activation trigger 260 may be located on a top portion of the main beam 264, or on an extension beam 266, which spaces the handle 108 from the shroud 112. As another example, the activation trigger 260 may be located on a portion of the shroud 112.

Figure 24:
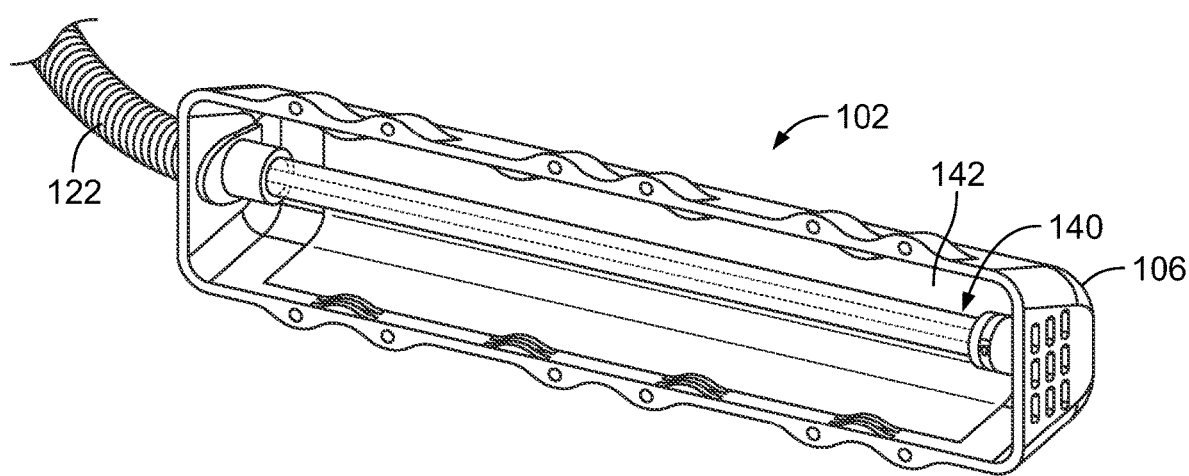
FIG. 24 illustrates a perspective bottom view of the wand assembly of FIG. 23.

FIG. 24 illustrates a perspective bottom view of the wand assembly 102 of FIG. 23. As shown, the reflector 142 is secured to an underside of the shroud 112.

Figure 25:
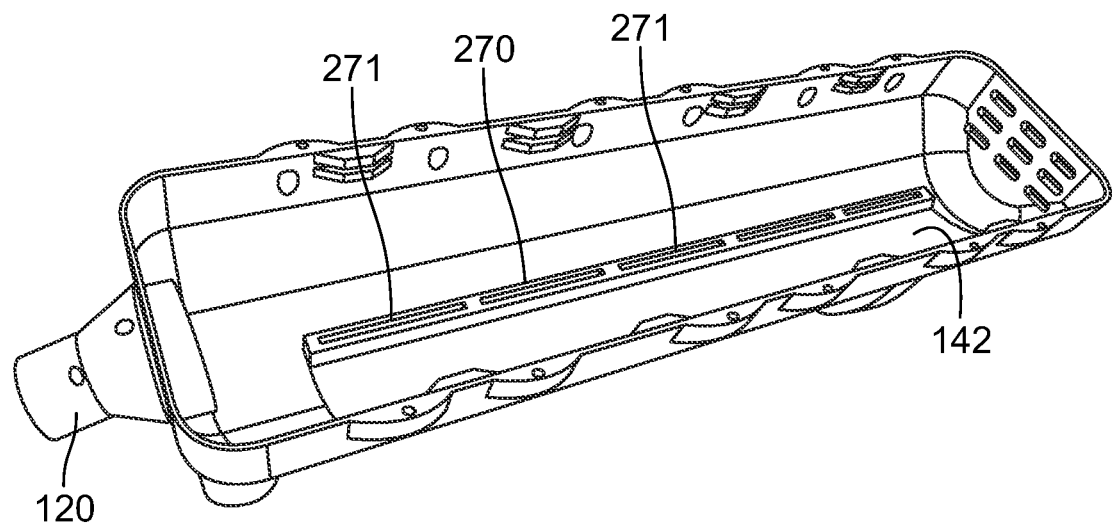
FIG. 25 illustrates a perspective bottom view of the wand assembly of FIGS. 23 and 24 without the UV lamp, according to an embodiment of the present disclosure.
Figure 26:
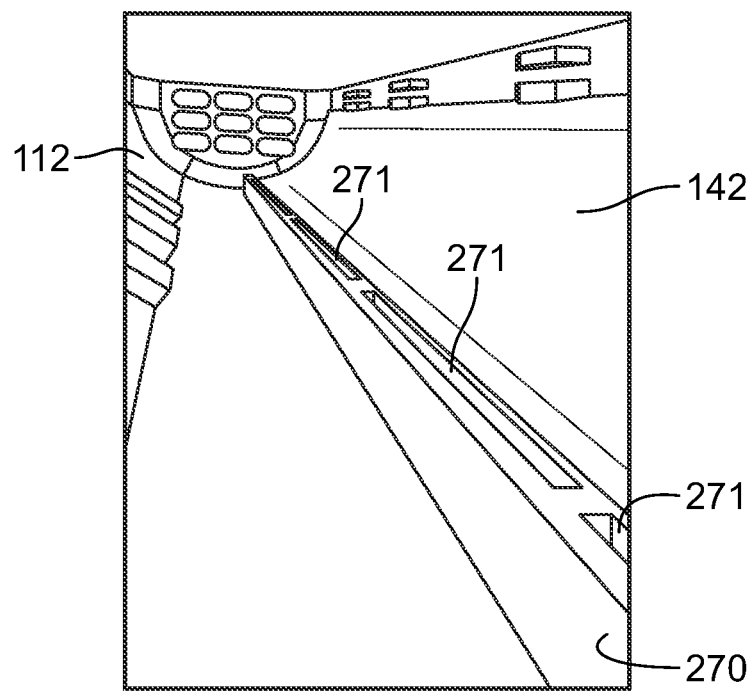
FIG. 26 illustrates a perspective view of a cooling manifold of a shroud of the wand assembly, according to an embodiment of the present disclosure.

FIG. 25 illustrates a perspective bottom view of the wand assembly 102 of FIGS. 23 and 24 without the UV lamp 140 (for the sake of clarity), according to an embodiment of the present disclosure. FIG. 26 illustrates a perspective view of a cooling manifold 270 of the shroud 112 of the wand assembly 102. Referring to FIGS. 25 and 26, a half of the reflector 142 is removed to expose a cooling manifold 270 that extends through the shroud 112 and is in fluid communication with the port 120. The cooling manifold 270 has a plurality of air outlets 271 that allow air delivered through the hose 122 (shown in FIG. 23, for example) that is coupled to the port 120 to pass over the UV lamp 140 when activated. In this manner, the UV lamp 140 is cooled during operation. The delivered air passes over and around the reflector 142 (which is disposed between the cooling manifold 270 and the UV lamp 140), through a channel defined through the reflector 142, and/or between two portions of the reflector 142 (such as a first half of the reflector 142 and a second half of the reflector 142).

As shown, the cooling manifold 270 is formed in the shroud 112. In at least one embodiment, the sanitizing head 106 including the shroud 112 is part of the wand assembly 102 of a portable sanitizing system. In at least one other embodiment, the sanitizing head 106 including the shroud 112 can be part of a permanent fixed sanitizing system. For example, the sanitizing head 106 including the shroud 112 can be part of a fixed and/or permanent sanitizing system within a lavatory, a galley or the like within an internal cabin of a vehicle, and/or within an enclosed space of a vehicle or fixed building, for example.

In at least one embodiment, a sanitizing system, such as the portable sanitizing system 100, includes the wand assembly 102. The wand assembly 102 includes the UV lamp 140. The cooling manifold 270 is configured to allow air to blow across the UV lamp 140, such as one or more bulbs of the UV lamp 140. The wand assembly 102 may also include a two-piece reflector 142, a master power switch, and a trigger switch, such as the activation trigger 260, to activate and illuminate the UV lamp 140.

During use of the wand assembly 102, the case assembly 200 may be placed away from the area being disinfected, thereby allowing the operator to transport only the wand assembly 102 to the area, and facilitating movement and operation in tight or confined spaces. The wand assembly 102 may include a 300 watt, 222 nm UV lamp, optional ranging lights, the cooling manifold 270 running the length of the shroud 112, the reflector 142, mounts (such as brackets, clamps, fasteners, and/or the like) to secure the UV lamp 140 to the shroud 112, a master power switch on the handle 108, and the activation trigger 260 on the handle 108 that is configured to be engaged to selectively activate and deactivate the UV lamp 140. The reflector 142 may be made out of Teflon or an aluminum sheet, which allows the reflector 142 to provide electromagnetic shielding. The UV lamp 140 may be attached to the shroud 112 with wire straps or bands, which may be positioned on top of Teflon tape and dry woven fiberglass that serve as a cushion between the strap and the glass bulb.

Figure 27:
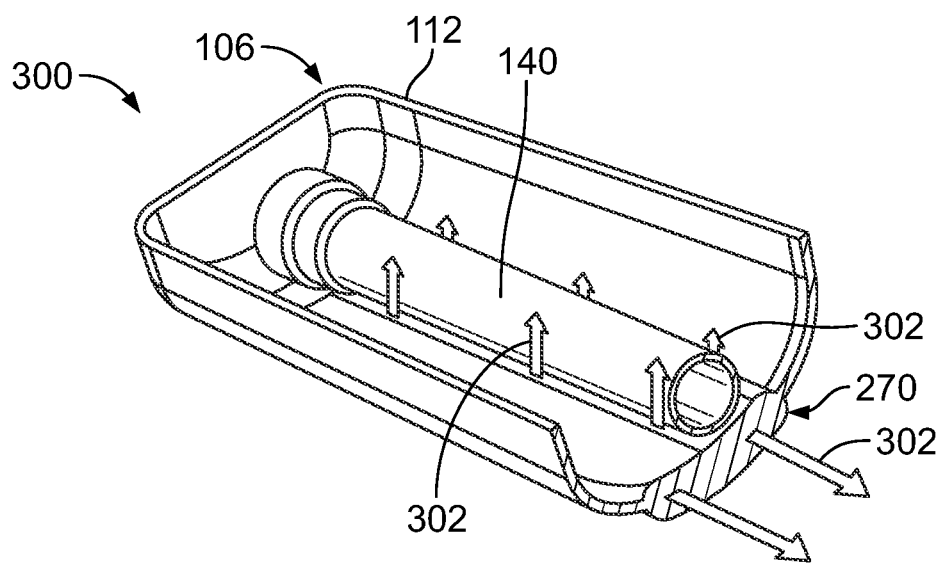
FIG. 27 illustrates a perspective bottom view of a portion of a sanitizing system, according to an embodiment of the present disclosure.

FIG. 27 illustrates a perspective bottom view of a portion of a sanitizing system 300, according to an embodiment of the present disclosure. The sanitizing system 300 includes the sanitizing head 106. For example, the sanitizing head 106 includes the UV lamp 140 secured within the shroud 112. In at least one embodiment, the sanitizing head 106 is part of a wand assembly, such as any of the wand assemblies described herein, and the sanitizing system 300 is a portable sanitizing system, such as any of the portable sanitizing systems described herein. The wand assembly can be coupled to a backpack assembly, a case assembly, a cart, and/or the like. In at least one other embodiment, the sanitizing head 106 is a fixture within an enclosed space. For example, the sanitizing head 106 can be fixed within an enclosed space, such as a lavatory, galley, or the like.

The UV lamp 140 includes one or more UV light emitters. The UV lamp 140 can be an integral structure. Optionally, the UV lamp 140 can include a plurality of UV modules.

The sanitizing system 300 includes a cooling manifold 270, such as described with respect to FIGS. 25 and 26. The cooling manifold 270 is configured to deliver air 302 around the UV lamp 140. The air 302 cools the UV lamp 140 as the UV lamp 140 emits UV light. Further, the cooling manifold 270 is also configured to direct air 302 out through the cooling manifold 270 to exhaust the air 302 and generated ozone through an exhaust, for example.

The cooling manifold 270 can be integrally formed with the shroud 112. In at least one other embodiment, the cooling manifold 270 is coupled to the shroud 112. The cooling manifold 270 can be disposed in various areas, such as within a lavatory, galley, flight deck, or various areas within a vehicle, fixed building, or the like.

Figure 28:
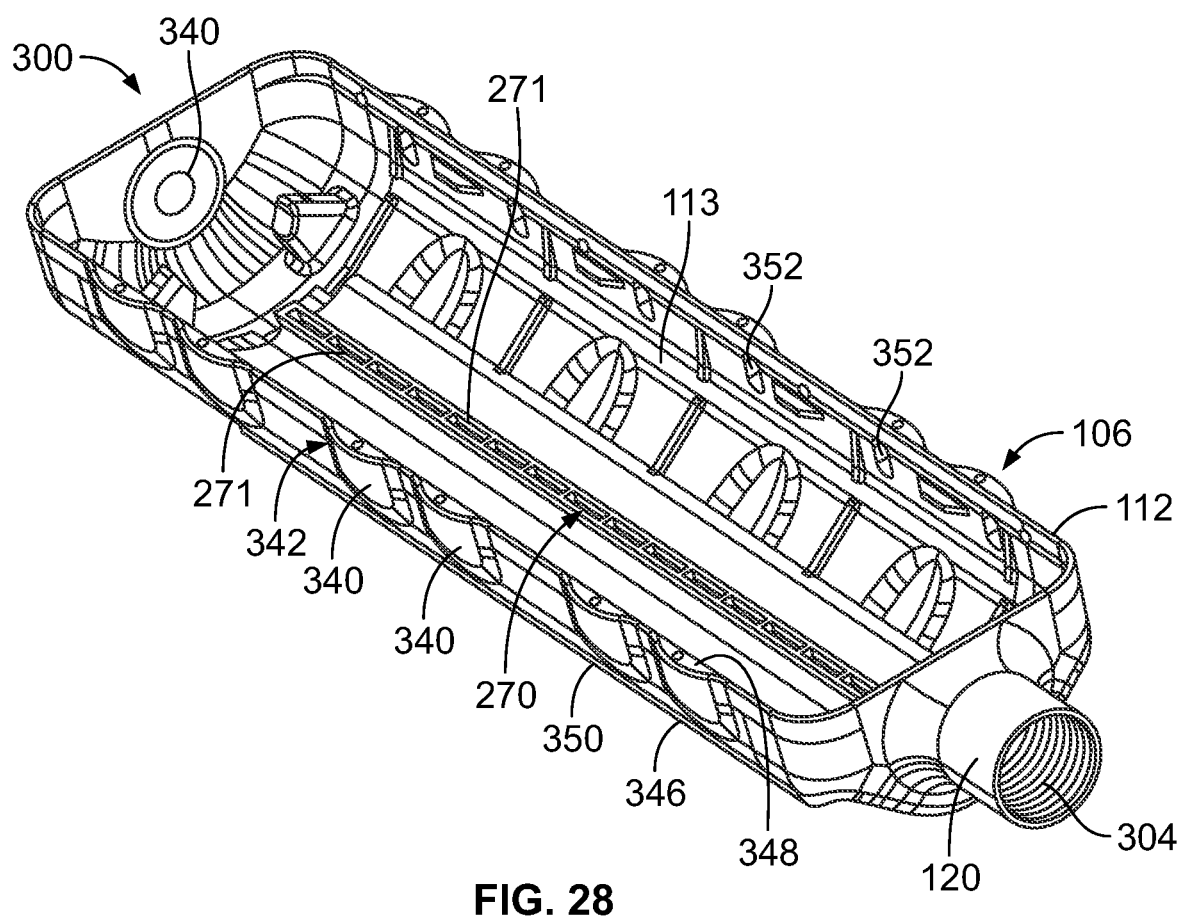
FIG. 28 illustrates a perspective bottom view of a shroud, according to an embodiment of the present disclosure.

FIG. 28 illustrates a perspective bottom view of the shroud 112, according to an embodiment of the present disclosure. As shown, the cooling manifold 270 is formed in the shroud 112. The UV lamp 140 (not shown in FIG. 28) is secured below (or over) the cooling manifold 270.

In at least one embodiment, the cooling manifold 270 includes a plurality of air outlets 271. The air outlets 271 can be linearly aligned. For example, the cooling manifold 270 includes a linear array of rectangular air outlets 271, such as slots. As another option, instead of a plurality of air outlets 271, a single long air outlet 271 can be used.

The port 120 includes a channel 304 that is in fluid communication with the cooling manifold 270. As noted, the port 120 is configured to couple to the hose 122 (shown in FIG. 2, for example). The hose 122 can be coupled to a backpack assembly, a cart, a case assembly, or the like that that includes a fan, blower, or the like. In at least one other embodiment, the hose 122 can be coupled to a fixed fan or blower, such as within an enclosed space.

Air is delivered to the cooling manifold 270 through the port 120. The air radially passes around the UV lamp 140. The port 120 may also allow air and ozone to be exhausted therethrough. The shroud 112 can also include exhaust ports that allow generated ozone to pass therethrough.

Figure 29:
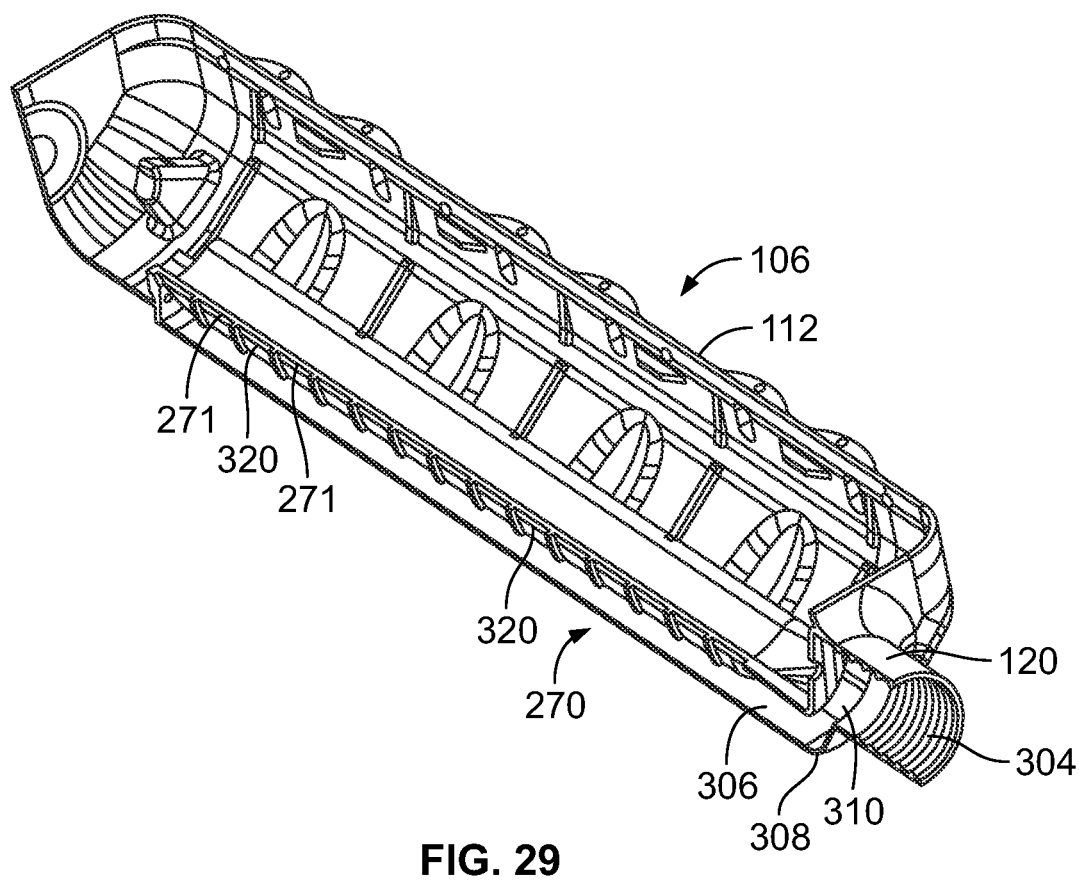
FIG. 29 illustrates a perspective cross-sectional view of a cooling manifold within the shroud of FIG. 28.
Figure 30:
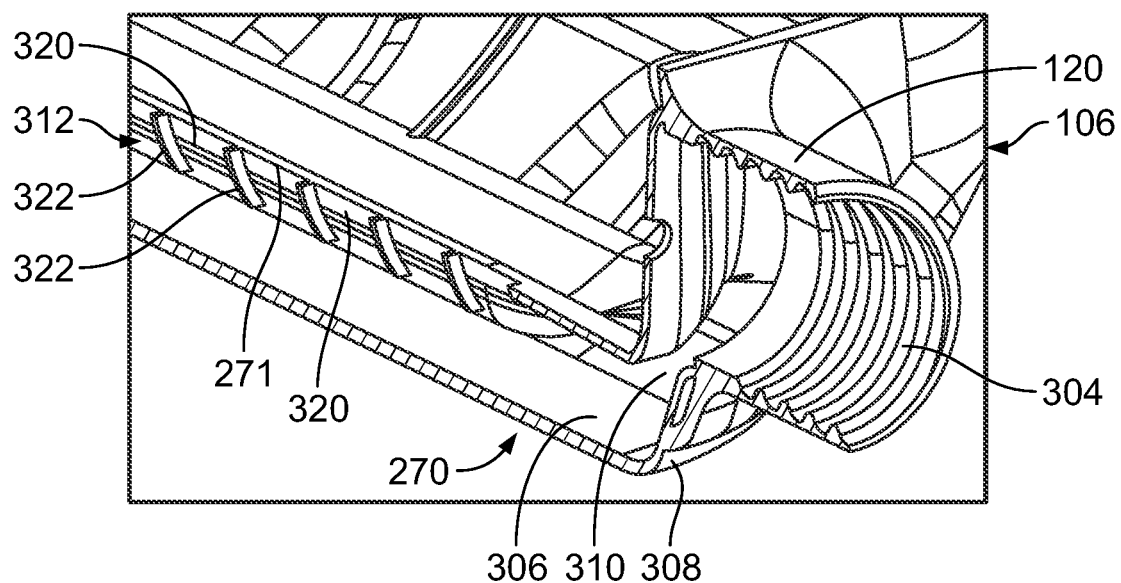
FIG. 30 illustrates a perspective cross-sectional view of directing slots of the cooling manifold, according to an embodiment of the present disclosure.
Figure 31:
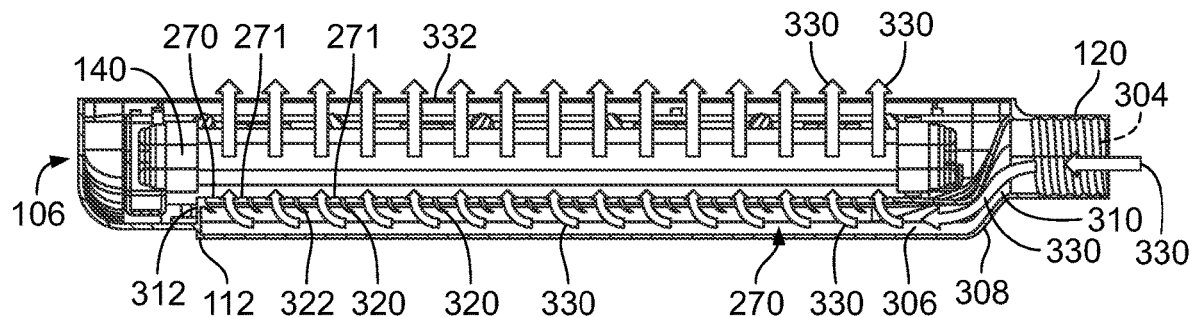
FIG. 31 illustrates a lateral internal view of the shroud of FIG. 28.

FIG. 29 illustrates a perspective cross-sectional view of the cooling manifold 270 within the shroud 112 of FIG. 28. FIG. 30 illustrates a perspective cross-sectional view of directing slots 320 of the cooling manifold 270, according to an embodiment of the present disclosure. FIG. 31 illustrates a lateral internal view of the shroud 112 of FIG. 28. Referring to FIGS. 28-31, the cooling manifold 270 includes a plenum 306 defined by walls 308. The walls 308 can be part of the shroud 112. As shown, the cooling manifold 270 is disposed over (or under, depending on the orientation) of an air delivery line 312, which is, in turn, disposed over (or under, depending on the orientation) of the air outlets 271.

The plenum 306 is in fluid communication with the channel 304 of the port 120 through a connecting conduit 310, such as defined by walls 308. The plenum 306 is disposed adjacent to an air delivery line 312. The air delivery line 312 fluidly couples the plenum 306 to the air outlets 271.

The air delivery line 312 includes the directing slots 320. The directing slots 320 are defined by arcuate fins 322. The arcuate fins 322 can be semi-circular in shape. A directing slot 320 is defined between two neighboring fins 322. Each directing slot 320 fluidly couples to a respective air outlet 271. The cooling manifold 270 may include more or less air outlets 271 and directing slots 320 than shown. Optionally, the air delivery line 312 may not include the directing slots 320. Instead, the plenum 306 can be fluidly coupled to the air outlets 271 without the directing slots 320.

In operation, cooling air 330 is supplied to the cooling manifold 270 through the channel 304 of the port 120. The air 330 pass through the channel 304, into the connecting conduit 310, and into the plenum 306. The air 330 is forced and/or otherwise directed via a fan or blower, for example. The air 330 within the plenum 306 then passes through the air delivery line 312 and out through the air outlets 271 around the UV lamp 140 to cool the UV lamp 140.

The arcuate fins 322 provide curved, arcuate directing slots 320 that direct the forced air 330 around the UV lamp 140. For example, the curved shape of the fins 322 provides an arcuate airflow around the UV lamp 140, thereby providing effective and even cooling around the UV lamp 140.

The directing slots 320 are sized, shaped, and configured to push air radially around the UV lamp 140. The directing slots 320 help create a jet of airflow. The directing slots 320 provide vanes that can be turned at an angle (for example, the fins 322 can be angled) so that the air flows around the UV lamp 140 over a desired path, so as to provide uniform cooling and along the length of the bulb (as opposed to just pushing fan air along a side or end of the UV lamp 140).

The forced air 330 cools the UV lamp 140 and passes through one or more openings 332 formed through the shroud 112. In this manner, the forced air 330 forces any generated ozone within the shroud 112 out through the openings 332, thereby ensuring that ozone concentration is low. As such, the cooling manifold 270 ensures that any ozone generated by operation of the UV lamp 140 is safely dispersed.

The cooling manifold 270 ensures that the air 330 is more uniformly distributed along the length of the UV lamp 140. Accordingly, the cooling manifold 270 ensures effective and efficient cooling of the UV lamp 140.

Referring again to FIG. 28, an exhaust port 340 can be formed in the shroud 112. The exhaust port 340 can be at an opposite end of the shroud 112 from the port 120. Additional exhaust ports 340 can be formed in the shroud 112. The exhaust port 340 can be formed at various other areas of the shroud 112. The exhaust port 340 is configured to allow air and ozone to be exhausted from the shroud 112.

In at least one embodiment, an exhaust manifold 342 is formed around a periphery of the shroud 112. The exhaust manifold 342 includes a plurality of exhaust ports 340 in fluid communication with an interior of the shroud 112, such as through one or more ducts. The exhaust manifold 342 may be along both sides of the shroud 112. The exhaust manifold 342 allows air and any generated ozone within the shroud 112 to be uniformly exhausted out of the shroud 112.

Each exhaust port 340 can include a hood 346 having an open end 348. An aperture 350 is formed through the open end 348. The aperture 350 is in fluid communication with an exhaust duct, passage, or the like that is in fluid communication with the internal chamber of the shroud 112. For example, each aperture 350 is in fluid communication with an opening 352 that is in fluid communication with the internal chamber 113 of the shroud 112. Optionally, the shroud 112 may not include the exhaust manifold 342 and/or separate exhaust ports 340.

The shroud 112 can further include a cover plate, such as the cover plate 154 described with respect to FIG. 14. In at least one other embodiment, the shroud 112 does not include a cover plate.

Figure 32:
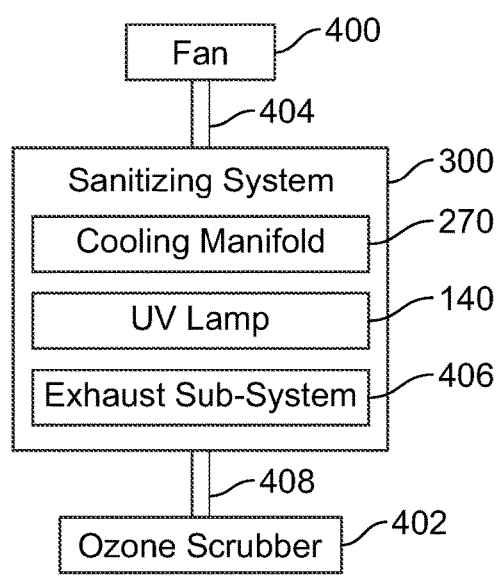
FIG. 32 illustrates a schematic block diagram of a sanitizing system coupled to a fan and an ozone scrubber, according to an embodiment of the present disclosure.

FIG. 32 illustrates a schematic block diagram of the sanitizing system 300 coupled to a fan 400 and an ozone scrubber 402, according to an embodiment of the present disclosure. In at least one embodiment, the sanitizing system 300 is distinct from the fan 400 and the ozone scrubber 402. In at least one other embodiment, the sanitizing system 300 includes one or both of the fan 400 and/or the ozone scrubber 402, such as within a backpack assembly, a case assembly, a cart, and/or the like.

The fan 400 is in fluid communication with the cooling manifold 270 (such as any of those described herein) through one or more conduits 404, such as one or more hoses, one or more tubes, one or more ducts, and/or the like. The fan 400 produces airflow that generates forced air into the cooling manifold 270, which cools the UV lamp 140, as described herein. The sanitizing system 300 can also include an exhaust sub-system 406, such as one or exhaust ports, an exhaust manifold, or the like, as described herein.

The air cools the UV lamp 140, and is exhausted, along with any generated ozone, through the exhaust sub-system 406. The exhaust sub-system 406 can, in turn, be in fluid communication with the ozone scrubber 402, such as through one or more conduits 408. The ozone scrubber 402 neutralizes, deactivates, and/or converts the ozone to air, for example. The scrubbed air can then be recirculated within an enclosed spacer, such as through an environmental control system, air conditioning system, and/or the like. Optionally, the sanitizing system 300 may not be coupled to the ozone scrubber 402.

In at least one embodiment, the sanitizing system 300 can be used to sanitize components within an enclosed space, such as flight deck of an aircraft. For example, the sanitizing system 300 can include a wand assembly, as described herein. The sanitizing system 300 can be used to reduce or otherwise displace ozone concentration levels during use. For example, a backpack or case assembly of the sanitizing system 300 can be placed outside an enclosed space (such as the flight deck), which allows the fan 400 to draw in air. While using the wand assembly in the enclosed space (the door to the enclosed space can be slightly propped open due to the hose extending therethrough), the wand assembly exhausts the ozone via the exhaust sub-system 406, while supplying cool air to the UV lamp 140 via the cooling manifold 270. The exhaust sub-system 406 may push the exhausted air into the enclosed space, which is then naturally drawn through the opened door. Accordingly, the ozone is displaced and dispersed out of the enclosed space.

Referring to FIGS. 1-32, certain embodiments of the present disclosure provide a sanitizing system including a sanitizing head 106. The sanitizing head 106 includes the UV lamp 140. The cooling manifold 270 is configured to deliver air to the UV lamp 140 to cool the UV lamp 140. In at least one embodiment, the sanitizing head 106 also includes the exhaust sub-system 406 that is configured to exhaust ozone from the sanitizing head 106.

Figure 33:
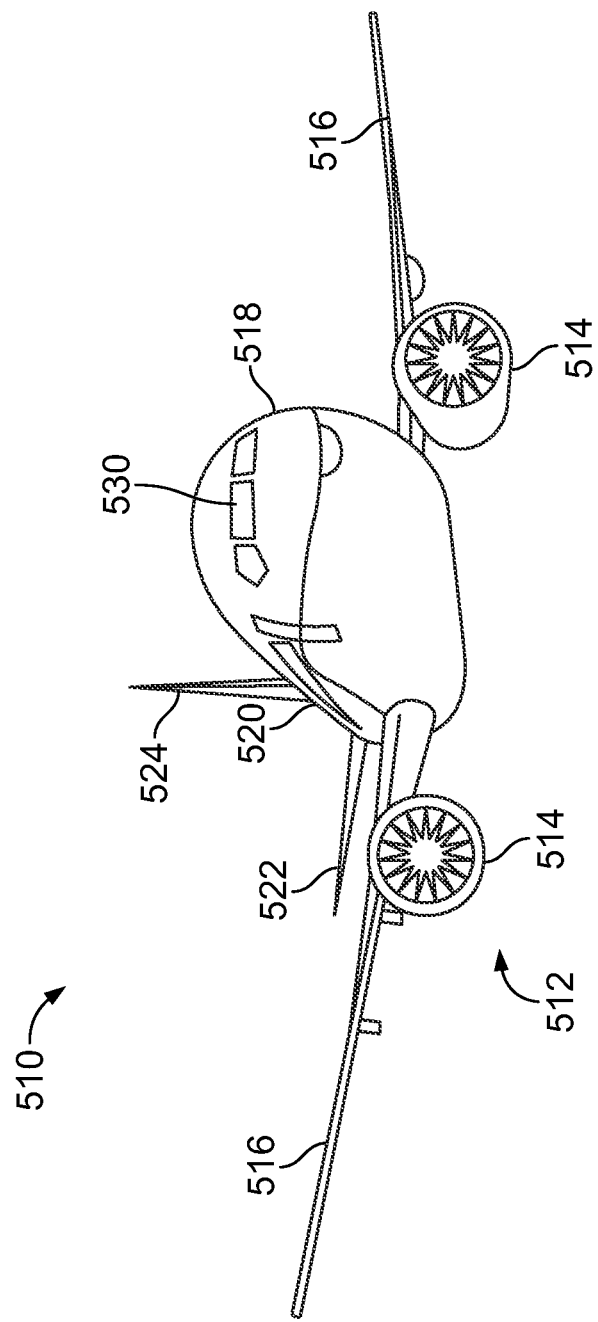
FIG. 33 illustrates a perspective front view of an aircraft, according to an embodiment of the present disclosure.

FIG. 33 illustrates a perspective front view of an aircraft 510, according to an embodiment of the present disclosure. The aircraft 510 includes a propulsion system 512 that includes engines 514, for example. Optionally, the propulsion system 512 may include more engines 514 than shown. The engines 514 are carried by wings 516 of the aircraft 510. In other embodiments, the engines 514 may be carried by a fuselage 518 and/or an empennage 520. The empennage 520 may also support horizontal stabilizers 522 and a vertical stabilizer 524.

The fuselage 518 of the aircraft 510 defines an internal cabin 530, which includes a flight deck or cockpit, one or more work sections (for example, galleys, personnel carry-on baggage areas, and the like), one or more passenger sections (for example, first class, business class, and coach sections), one or more lavatories, and/or the like.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings. In general, the sanitizing systems described herein may be used to sanitizing various components, such as within enclosed spaces, outdoor spaces, and the like.

Figure 34A:
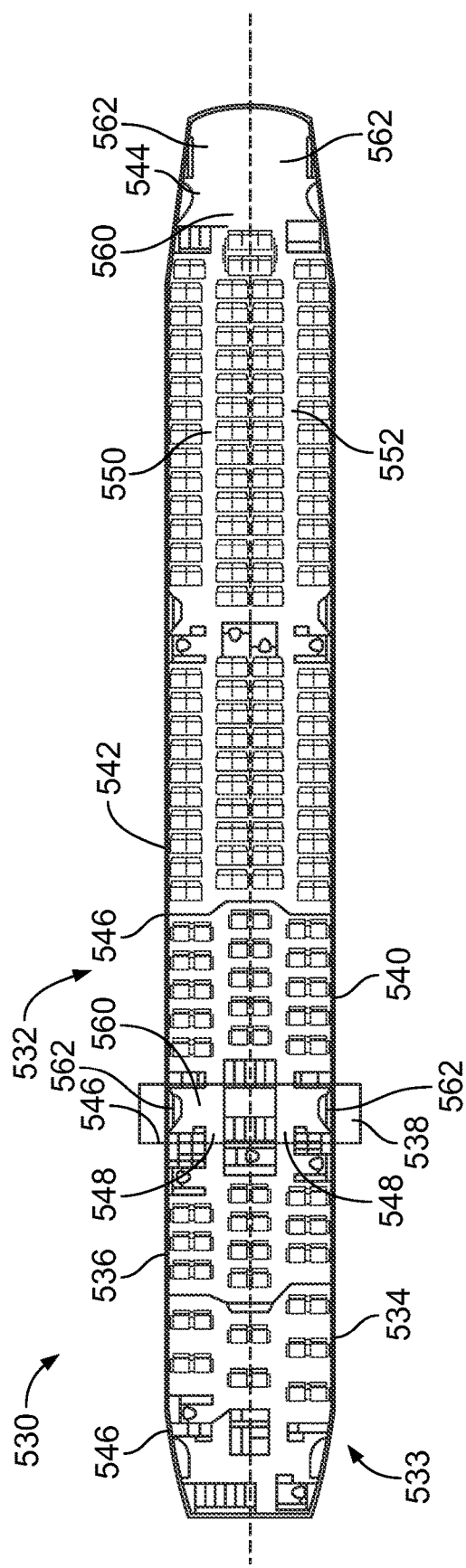
FIG. 34A illustrates a top plan view of an internal cabin of an aircraft, according to an embodiment of the present disclosure.

FIG. 34A illustrates a top plan view of an internal cabin 530 of an aircraft, according to an embodiment of the present disclosure. The internal cabin 530 may be within the fuselage 532 of the aircraft, such as the fuselage 518 of FIG. 33. For example, one or more fuselage walls may define the internal cabin 530. The internal cabin 530 includes multiple sections, including a front section 533, a first-class section 534, a business class section 536, a front galley station 538, an expanded economy or coach section 540, a standard economy of coach section 542, and an aft section 544, which may include multiple lavatories and galley stations. It is to be understood that the internal cabin 530 may include more or less sections than shown. For example, the internal cabin 530 may not include a first-class section, and may include more or less galley stations than shown. Each of the sections may be separated by a cabin transition area 546, which may include class divider assemblies between aisles 548.

As shown in FIG. 34A, the internal cabin 530 includes two aisles 550 and 552 that lead to the aft section 544. Optionally, the internal cabin 530 may have less or more aisles than shown. For example, the internal cabin 530 may include a single aisle that extends through the center of the internal cabin 530 that leads to the aft section 544.

The aisles 548, 550, and 552 extend to egress paths or door passageways 560. Exit doors 562 are located at ends of the egress paths 560. The egress paths 560 may be perpendicular to the aisles 548, 550, and 552. The internal cabin 530 may include more egress paths 560 at different locations than shown. The sanitizing systems shown and described with respect to FIGS. 1-32 may be used to sanitize various structures within the internal cabin 530, such as passenger seats, monuments, stowage bin assemblies, components on and within lavatories, galley equipment and components, and/or the like.

Figure 34B:
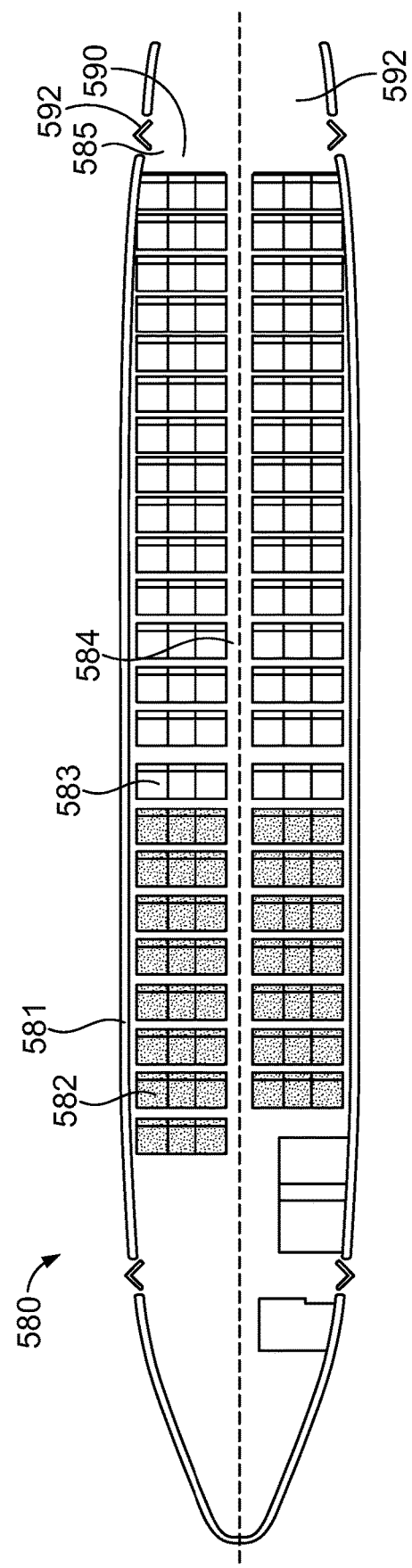
FIG. 34B illustrates a top plan view of an internal cabin of an aircraft, according to an embodiment of the present disclosure.

FIG. 34B illustrates a top plan view of an internal cabin 580 of an aircraft, according to an embodiment of the present disclosure. The internal cabin 580 is an example of the internal cabin 530 shown in FIG. 33. The internal cabin 580 may be within a fuselage 581 of the aircraft. For example, one or more fuselage walls may define the internal cabin 580. The internal cabin 580 includes multiple sections, including a main cabin 582 having passenger seats 583, and an aft section 585 behind the main cabin 582. It is to be understood that the internal cabin 380 may include more or less sections than shown.

The internal cabin 580 may include a single aisle 584 that leads to the aft section 585. The single aisle 584 may extend through the center of the internal cabin 580 that leads to the aft section 585. For example, the single aisle 584 may be coaxially aligned with a central longitudinal plane of the internal cabin 580.

The aisle 584 extends to an egress path or door passageway 590. Exit doors 592 are located at ends of the egress path 590. The egress path 590 may be perpendicular to the aisle 584. The internal cabin 580 may include more egress paths than shown. The sanitizing systems shown and described with respect to FIGS. 1-32 may be used to sanitize various structures within the internal cabin 530, such as passenger seats, monuments, stowage bin assemblies, components on and within lavatories, galley equipment and components, and/or the like.

Figure 35:
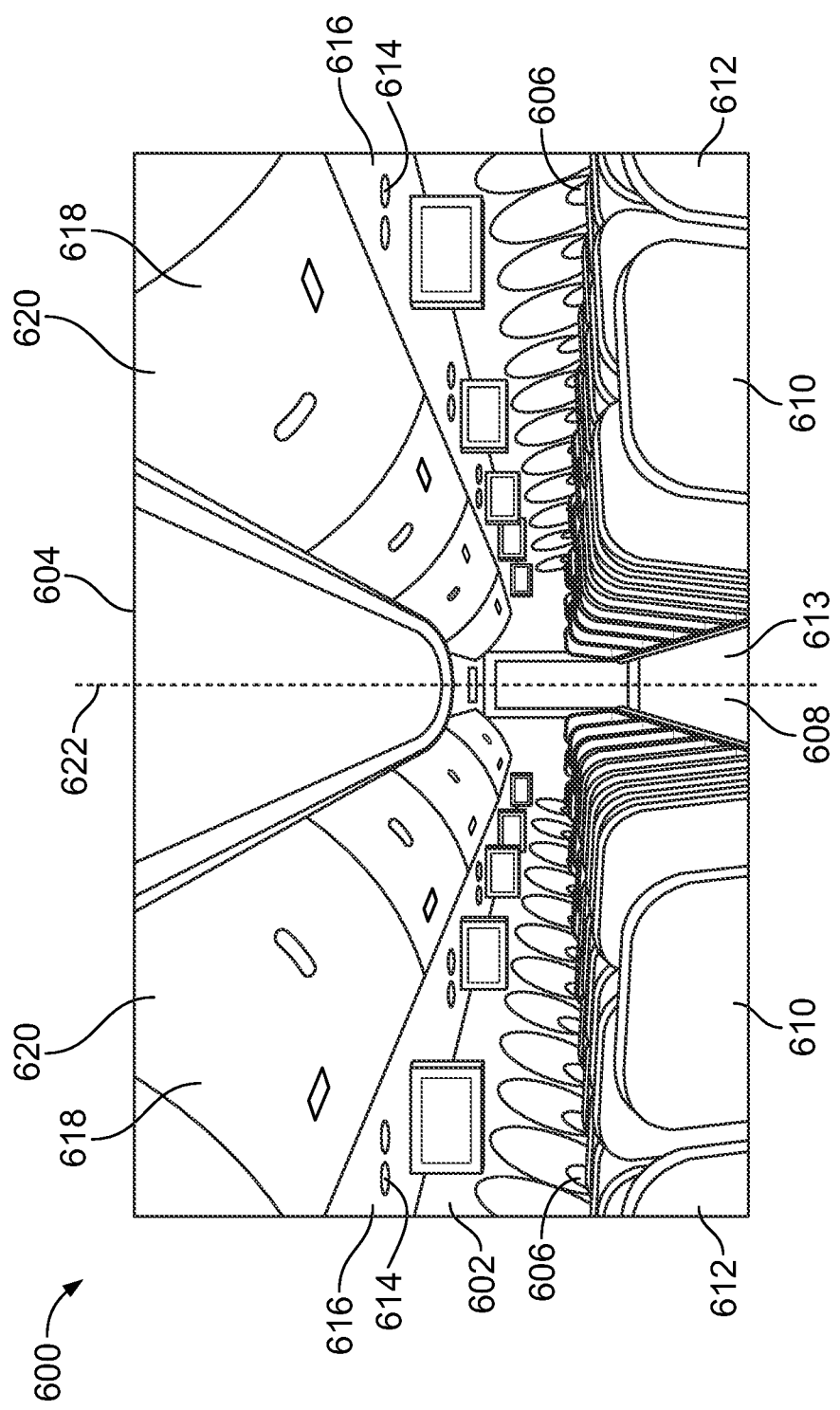
FIG. 35 illustrates a perspective interior view of an internal cabin of an aircraft, according to an embodiment of the present disclosure.

FIG. 35 illustrates a perspective interior view of an internal cabin 600 of an aircraft, according to an embodiment of the present disclosure. The internal cabin 600 includes outboard walls 602 connected to a ceiling 604. Windows 606 may be formed within the outboard walls 602. A floor 608 supports rows of seats 610. As shown in FIG. 35, a row 612 may include two seats 610 on either side of an aisle 613. However, the row 612 may include more or less seats 610 than shown. Additionally, the internal cabin 600 may include more aisles than shown.

Passenger service units (PSUs) 614 are secured between an outboard wall 602 and the ceiling 604 on either side of the aisle 613. The PSUs 614 extend between a front end and rear end of the internal cabin 600. For example, a PSU 614 may be positioned over each seat 610 within a row 612. Each PSU 614 may include a housing 616 that generally contains vents, reading lights, an oxygen bag drop panel, an attendant request button, and other such controls over each seat 610 (or groups of seats) within a row 612.

Overhead stowage bin assemblies 618 are secured to the ceiling 604 and/or the outboard wall 602 above and inboard from the PSU 614 on either side of the aisle 613. The overhead stowage bin assemblies 618 are secured over the seats 610. The overhead stowage bin assemblies 618 extend between the front and rear end of the internal cabin 600. Each stowage bin assembly 618 may include a pivot bin or bucket 620 pivotally secured to a strongback (hidden from view in FIG. 35). The overhead stowage bin assemblies 618 may be positioned above and inboard from lower surfaces of the PSUs 614. The overhead stowage bin assemblies 618 are configured to be pivoted open in order to receive passenger carry-on baggage and personal items, for example.

As used herein, the term "outboard" means a position that is further away from a central longitudinal plane 622 of the internal cabin 600 as compared to another component. The term "inboard" means a position that is closer to the central longitudinal plane 622 of the internal cabin 600 as compared to another component. For example, a lower surface of a PSU 614 may be outboard in relation to a stowage bin assembly 618.

The sanitizing systems shown and described with respect to FIGS. 1-32 may be used to sanitize various structures shown within the internal cabin 600.

When not in use, a portable sanitizing system may be stored within a closet, galley cart bay, or galley cart, such as within the internal cabin of the vehicle.

Figure 36:
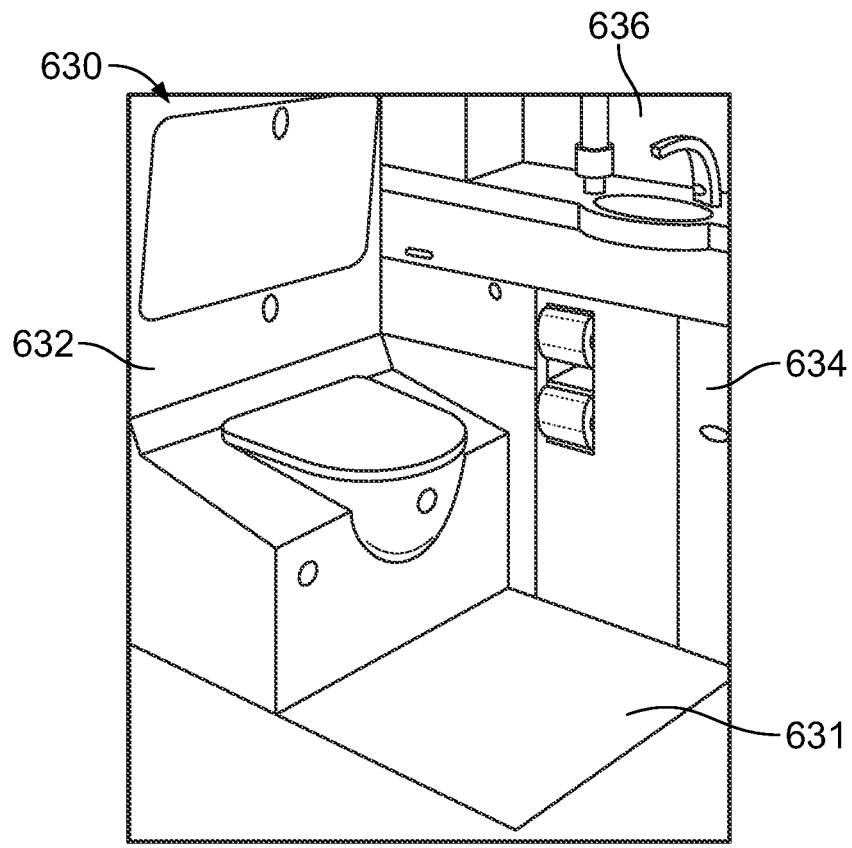
FIG. 36 illustrates a perspective internal view of a lavatory within an internal cabin of an aircraft.

FIG. 36 illustrates a perspective internal view of a lavatory 630 within an internal cabin of a vehicle, such as any of the internal cabins described herein. The lavatory 630 is an example of an enclosed space, monument or chamber, such as within the internal cabin a vehicle. The lavatory 630 may be onboard an aircraft, as described above. Optionally, the lavatory 630 may be onboard various other vehicles. In other embodiments, the lavatory 630 may be within a fixed structure, such as a commercial or residential building. The lavatory 630 includes a base floor 631 that supports a toilet 632, cabinets 634, and a sink 636 or wash basin. The lavatory 630 may be arranged differently than shown. The lavatory 630 may include more or less components than shown. The sanitizing systems shown and described with respect to FIGS. 1-32 may be used to sanitize the various structures, components, and surfaces within the lavatory 630.

The sanitizing systems as described herein can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the sanitizing systems are used to augment a cleaning process, such as after manual cleaning.

Figure 37:
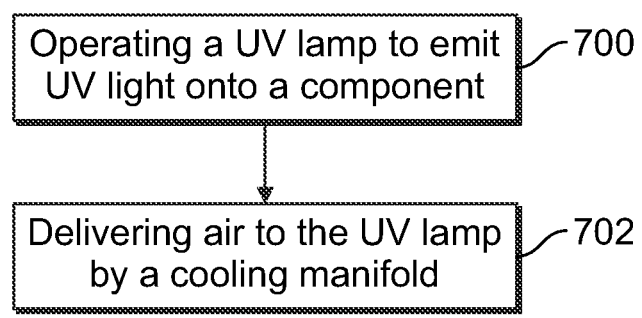
FIG. 37 illustrates a flow chart of a sanitizing method, according to an embodiment of the present disclosure.

FIG. 37 illustrates a flow chart of a sanitizing method, according to an embodiment of the present disclosure. The sanitizing method includes operating, at 700, an ultraviolet (UV) lamp of a sanitizing head to emit UV light onto a component; and delivering, at 702, air to the UV lamp by a cooling manifold.

In at least one embodiment, the sanitizing method includes disposing the sanitizing head within a wand assembly. As a further example, the method includes coupling the wand assembly to one of a backpack assembly or a case assembly.

In at least one embodiment, said delivering comprises passing, through one or more air outlets of the cooling manifold, the air onto and around the UV lamp.

In at least one example, the method further includes fluidly coupling a channel of a port having with the cooling manifold.

In at least one embodiment, said delivering includes directing the air to one or more air outlets through one or more directing slots defined by one or more arcuate fins.

In at least one example, the sanitizing method further includes exhausting one or more gases (such as air and/or ozone) through an exhaust sub-system of the sanitizing head.

Further, the disclosure comprises embodiments according to the following clauses:

Clause 1. A sanitizing system, comprising:
a sanitizing head including:
an ultraviolet (UV) lamp; and
a cooling manifold configured to deliver air to the UV lamp.

Clause 2. The sanitizing system of Clause 1, further comprising a wand assembly, wherein the wand assembly includes the sanitizing head.

Clause 3. The sanitizing system of Clause 2, wherein the sanitizing system further comprises a backpack assembly coupled to the wand assembly.

Clause 4. The sanitizing system of Clause 2, wherein the sanitizing system further comprises a case assembly coupled to the wand assembly.

Clause 5. The sanitizing system of any of Clauses 1-4, wherein the sanitizing head is a fixture within an enclosed space.

Clause 6. The sanitizing system of any of Clauses 1-5, wherein the cooling manifold comprises one or more air outlets configured to pass the air onto and around the UV lamp.

Clause 7. The sanitizing system of any of Clauses 1-6, wherein the sanitizing head comprises a shroud, and wherein the cooling manifold is formed within the shroud.

Clause 8. The sanitizing system of any of Clauses 1-7, further comprising a port having a channel in fluid communication with the cooling manifold.

Clause 9. The sanitizing system of Clause 8, wherein the cooling manifold comprises:
- a plenum;
- a connecting conduit that fluidly couples the plenum to the channel;
- an air delivery line in fluid communication with the plenum; and
- one or more air outlets in fluid communication with the air delivery line.

Clause 10. The sanitizing system of any of Clauses 1-9, wherein the cooling manifold comprises:
- one or more directing slots defined by one or more arcuate fins; and
- one or more air outlets fluid coupled to the one or more directing slots.

Clause 11. The sanitizing system of any of Clauses 1-10, further comprising an exhaust sub-system.

Clause 12. The sanitizing system of Clause 11, wherein the exhaust sub-system comprises one or more exhaust ports formed in a shroud of the sanitizing head.

Clause 13. A sanitizing method, comprising:
- operating an ultraviolet (UV) lamp of a sanitizing head to emit UV light onto a component; and
- delivering air to the UV lamp by a cooling manifold.

Clause 14. The sanitizing method of Clause 13, further comprising disposing the sanitizing head within a wand assembly.

Clause 15. The sanitizing method of Clause 14, further comprising coupling the wand assembly to one of a backpack assembly or a case assembly.

Clause 16. The sanitizing method of any of Clauses 13-15, wherein said delivering comprises passing, through one or more air outlets of the cooling manifold, the air onto and around the UV lamp.

Clause 17. The sanitizing method of any of Clauses 13-16, further comprising fluidly coupling a channel of a port having with the cooling manifold.

Clause 18. The sanitizing method of any of Clauses 13-17, wherein said delivering comprises directing the air to one or more air outlets through one or more directing slots defined by one or more arcuate fins.

Clause 19. The sanitizing method of any of Clauses 13-18, further comprising exhausting one or more gases through an exhaust sub-system of the sanitizing head.

Clause 20. A sanitizing head of a sanitizing system, the sanitizing head comprising:
- an ultraviolet (UV) lamp;
- a port having a channel;
- an exhaust sub-system including one or more exhaust ports; and
- a cooling manifold configured to deliver air to the UV lamp, wherein the cooling manifold is in fluid communication with the channel, and wherein the cooling manifold comprises:
  - one or more air outlets configured to pass the air onto and around the UV lamp;
  - a plenum;
  - a connecting conduit that fluidly couples the plenum to the channel; and
  - an air delivery line in fluid communication with the plenum and the one or more air outlets.

As described herein, embodiments of the present disclosure provide systems and a methods for efficiently sanitizing surfaces, components, structures, and/or the like within an internal cabin of a vehicle. Further, embodiments of the present disclosure provide compact, easy-to-use, and safe systems and methods for using UV light to sanitize surfaces within an internal cabin.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system, comprising:
 a sanitizing head including:
  an ultraviolet (UV) lamp;
  a port having a channel; and
  a cooling manifold configured to deliver air to the UV lamp, wherein the cooling manifold is in fluid communication with the channel, and wherein the cooling manifold comprises:
   a plenum;
   a connecting conduit that fluidly couples the plenum to the channel;
   an air delivery line in fluid communication with the plenum; and
   one or more air outlets in fluid communication with the air delivery line.

2. The sanitizing system of claim 1, further comprising a wand assembly, wherein the wand assembly includes the sanitizing head.

3. The sanitizing system of claim 2, wherein the sanitizing system further comprises a backpack assembly coupled to the wand assembly.

4. The sanitizing system of claim 2, wherein the sanitizing system further comprises a case assembly coupled to the wand assembly.

5. The sanitizing system of claim 1, wherein the sanitizing head is a fixture within an enclosed space.

6. The sanitizing system of claim 1, wherein the one or more air outlets are configured to pass the air onto and around the UV lamp.

7. The sanitizing system of claim 1, wherein the sanitizing head further comprises a shroud, and wherein the cooling manifold is formed within the shroud.

8. The sanitizing system of claim 1, wherein the cooling manifold further comprises one or more directing slots defined by one or more arcuate fins, and wherein the one or more air outlets are fluidly coupled to the one or more directing slots.

9. The sanitizing system of claim 1, further comprising an exhaust sub-system.

10. The sanitizing system of claim 9, wherein the exhaust sub-system comprises one or more exhaust ports formed in a shroud of the sanitizing head.

11. A sanitizing method for a sanitizing system comprising:
 a sanitizing head including:
  an ultraviolet (UV) lamp;
  a port having a channel; and
  a cooling manifold configured to deliver air to the UV lamp, wherein the cooling manifold is in fluid communication with the channel, and wherein the cooling manifold comprises:
   a plenum;
   a connecting conduit that fluidly couples the plenum to the channel;
   an air delivery line in fluid communication with the plenum; and
   one or more air outlets in fluid communication with the air delivery line,
 the sanitizing method comprising:
  operating the UV lamp of the sanitizing head to emit UV light onto a component; and
  delivering the air to the UV lamp by the cooling manifold.

12. The sanitizing method of claim 11, further comprising disposing the sanitizing head within a wand assembly.

13. The sanitizing method of claim 12, further comprising coupling the wand assembly to one of a backpack assembly or a case assembly.

14. The sanitizing method of claim 11, wherein said delivering comprises passing, through the one or more air outlets of the cooling manifold, the air onto and around the UV lamp.

15. The sanitizing method of claim 11, wherein said delivering comprises directing the air to the one or more air outlets through one or more directing slots defined by one or more arcuate fins.

16. The sanitizing method of claim 11, further comprising exhausting one or more gases through an exhaust sub-system of the sanitizing head.

17. A sanitizing head of a sanitizing system, the sanitizing head comprising:
 an ultraviolet (UV) lamp;
 a port having a channel;
 an exhaust sub-system including one or more exhaust ports; and
 a cooling manifold configured to deliver air to the UV lamp, wherein the cooling manifold is in fluid communication with the channel, and wherein the cooling manifold comprises:
  one or more air outlets configured to pass the air onto and around the UV lamp;
  a plenum;
  a connecting conduit that fluidly couples the plenum to the channel; and
  an air delivery line in fluid communication with the plenum and the one or more air outlets.

18. The sanitizing head of claim 17, wherein the sanitizing head is a fixture within an enclosed space.

19. The sanitizing head of claim 17, wherein the sanitizing head further comprises a shroud, and wherein the cooling manifold is formed within the shroud.

20. The sanitizing head of claim 17, wherein the cooling manifold further comprises one or more directing slots defined by one or more arcuate fins, and wherein the one or more air outlets are fluidly coupled to the one or more directing slots.

* * * * *